US010158079B2

(12) United States Patent
Tierney et al.

(10) Patent No.: US 10,158,079 B2
(45) Date of Patent: Dec. 18, 2018

(54) POLYMERS OF BENZODITHIOPHENE AND THEIR USE AS ORGANIC SEMICONDUCTORS

(71) Applicant: Merck Patent GmbH, Darmstadt (DE)

(72) Inventors: Steven Tierney, Southampton (GB); Nicolas Blouin, Southampton (GB); William Mitchell, Chandler's Ford (GB); Changsheng Wang, Durham (GB); Miguel Carrasco-Orozco, Winchester (GB); Frank Egon Meyer, Winchester (GB)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 14/674,934

(22) Filed: Mar. 31, 2015

(65) Prior Publication Data
US 2015/0207076 A1 Jul. 23, 2015

Related U.S. Application Data

(62) Division of application No. 13/642,180, filed as application No. PCT/EP2011/001437 on Mar. 23, 2011, now Pat. No. 10,050,201.

(30) Foreign Application Priority Data

Apr. 19, 2010 (EP) .................... 10004148

(51) Int. Cl.
| H01L 51/00 | (2006.01) |
| C07D 495/04 | (2006.01) |
| C07D 519/00 | (2006.01) |
| H01B 1/12 | (2006.01) |
| C09B 69/10 | (2006.01) |
| C07D 498/04 | (2006.01) |
| C07D 513/04 | (2006.01) |
| C08G 75/32 | (2006.01) |
| C09K 11/06 | (2006.01) |
| H01L 51/42 | (2006.01) |
| C08G 61/12 | (2006.01) |
| C08G 75/00 | (2006.01) |

(52) U.S. Cl.
CPC ........ *H01L 51/0036* (2013.01); *C07D 495/04* (2013.01); *C07D 498/04* (2013.01); *C07D 513/04* (2013.01); *C07D 519/00* (2013.01); *C08G 61/126* (2013.01); *C08G 75/00* (2013.01); *C08G 75/32* (2013.01); *C09B 69/109* (2013.01); *C09K 11/06* (2013.01); *H01B 1/127* (2013.01); *H01L 51/0043* (2013.01); *C08G 2261/141* (2013.01); *C08G 2261/3243* (2013.01); *C08G 2261/411* (2013.01); *C08G 2261/414* (2013.01); *C08G 2261/91* (2013.01); *C08G 2261/92* (2013.01); *H01L 51/42* (2013.01); *Y02E 10/549* (2013.01)

(58) Field of Classification Search
CPC .. C07D 513/04; C07D 498/04; C07D 495/04; C07D 519/04; C07D 519/00; G08G 61/126; G08G 75/00; G08G 75/32; H01L 51/0036; H01L 51/0043; H01B 1/127; C09B 69/109; C09K 11/06; C08G 2261/91; C08G 2261/92; C08G 2261/411; C08G 2261/414; C08G 2261/141; C08G 2261/3243
See application file for complete search history.

(56) References Cited

U.S. PATENT DOCUMENTS

| 6,913,710 | B2 | 7/2005 | Farrand |
| 7,524,922 | B2 | 4/2009 | Heeney et al. |
| 8,101,776 | B2 | 1/2012 | Berens et al. |
| 8,304,512 | B2 | 11/2012 | Wigglesworth et al. |
| 8,334,456 | B2 | 12/2012 | Zhu et al. |
| 9,337,358 | B2 | 5/2016 | Byrne et al. |
| 2005/0082525 | A1 | 4/2005 | Heeney et al. |
| 2009/0299070 | A1 | 12/2009 | Berens et al. |
| 2009/0302311 | A1 | 12/2009 | Turbiez et al. |
| 2010/0007874 | A1 | 1/2010 | Lunati et al. |
| 2010/0078074 | A1 | 4/2010 | Yang et al. |
| 2010/0297405 | A1 | 11/2010 | Flores et al. |
| 2010/0307594 | A1* | 12/2010 | Zhu .............. B82Y 10/00 136/263 |
| 2011/0101329 | A1 | 5/2011 | Kastler et al. |
| 2011/0155248 | A1 | 5/2011 | Kastler et al. |
| 2011/0124822 | A1 | 6/2011 | Yu et al. |
| 2011/0168264 | A1 | 7/2011 | Kastler et al. |
| 2012/0187385 | A1 | 7/2012 | Pan et al. |
| 2012/0232237 | A1 | 9/2012 | Li et al. |

FOREIGN PATENT DOCUMENTS

| CN | 101875717 | 11/2010 |
| EP | 1524286 | * 9/2004 |

(Continued)

OTHER PUBLICATIONS

Hou, J. et al., "Synthesis of a Low Band Gap Polymer and its Application in Highly Efficient Polymer Solar Cell," J. Am. Chem. Soc., 2009, vol. 131, pp. 15580-15582.

(Continued)

*Primary Examiner* — Amina S Khan

(74) *Attorney, Agent, or Firm* — Millen, White, Zelano & Branigan, PC

(57) ABSTRACT

The invention relates to novel polymers of benzodithiophene, methods and materials for their preparation, their use as semiconductors in organic electronic (OE) devices, and to OE devices comprising these polymers.

16 Claims, No Drawings

(56) References Cited

FOREIGN PATENT DOCUMENTS

| | | | |
|---|---|---|---|
| EP | 1524286 | * | 4/2005 |
| EP | 1524286 A1 | | 4/2005 |
| EP | 1916250 | | 4/2008 |
| JP | 2001247576 | | 9/2001 |
| JP | 2005120379 | | 5/2005 |
| JP | 2012527784 | | 11/2012 |
| KR | 20100086197 | | 7/2010 |
| WO | 2007068618 | | 6/2007 |
| WO | 2008000664 | | 1/2008 |
| WO | 2009053291 | | 4/2009 |
| WO | 2010000669 | | 1/2010 |
| WO | 2010000670 | | 1/2010 |
| WO | 2010000755 | | 1/2010 |
| WO | 2010008672 | | 1/2010 |
| WO | 2010135701 | | 11/2010 |
| WO | 2011060526 | | 5/2011 |

OTHER PUBLICATIONS

Huo, L. et al., "A polybenzol[1,2-b: 4,5-b']dithiophene derivative with deep HOMO Level and its Application in High-Performance Polymer Solar Cells," Angew. Chem. Int. Ed., 2010, vol. 49, pp. 1500-1503.
International Search Report for PCT/EP2011/001437, Date of the actual completion of the international search: Jun. 17, 2011, International Search Report: dated Jul. 22, 2011.
Lee, J. M. et al., "Polytiophene derivative and organic thin film transistor using it," Publication Date: Jan. 22, 2009; English Abstract of KR-2010 086197.
Liang, Y. et al., "Control in Energy Levels of Conjugated Polymers for Photovoltaic Application," J. Phys. Chem., 2008, vol. 112, pp. 7866-7871.
Price, S. C. et al., "Low Band Gap Polymers Based on Benzol[1,2-b:4,5-b']dithiophene: Rational Design of Polymers Leads to High Photovoltaic Performance," Macromolecules, 2010, vol. 43, pp. 4609-4612.
TDK Corp, "Thiophene derivative and its polymer," Patent Abstracts of Japan, Publication Date: Sep. 11, 2011; English Abstract of JP-2001 247576.
Zou, Y. et al., "5,6-Octyloxydithienylbenzothiadiazole-dithienylbenzene copolymer," Publication Date: Jul. 20, 2010; English Abstract of CN-101875717.
English Translation Abstract of JP 2005-120379 published May 12, 2005.
English Translation Abstract of JP 2012-527784 published Nov. 8, 2012.
K. Shiraishi et al., "New π-Conjugated Polymers Constituted of Dialkoxybenzodithiophene Units: Synthesis and Electronic Properties", Synthetic Metals, vol. 130 (2002) pp. 139-147.
Office Action for corresponding Korean Patent Application No. 10-2012-7030150—Dated: Mar. 9, 2017.
Office Action for corresponding Indian Patent Application No. 3541/KOLNP/2012—Dated: Dec. 28, 2017.
D3-Hou et al; J. Phys. Chem C 2009, 113, 21202-21207 (2009).

* cited by examiner

POLYMERS OF BENZODITHIOPHENE AND THEIR USE AS ORGANIC SEMICONDUCTORS

FIELD OF THE INVENTION

The invention relates to novel polymers of benzodithiophene, methods and materials for their preparation, their use as semiconductors in organic electronic (OE) devices, and to OE devices comprising these polymers.

BACKGROUND OF THE INVENTION

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), photodetectors, organic photovoltaic (OPV) cells, sensors, memory elements and logic circuits to name just a few. The organic semiconducting materials are typically present in the electronic device in the form of a thin layer, for example less than 1 micron thick.

The performance of OFET devices is principally based upon the charge carrier mobility of the semiconducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semiconducting material is relatively stable to oxidation i.e. it has a high ionisation potential, as oxidation leads to reduced device performance. Further requirements for the semiconducting material are a good processability, especially for large-scale production of thin layers and desired patterns, and high stability, film uniformity and integrity of the organic semiconductor layer.

For application in bulk heterojunction (BHJ) organic photovoltaic (OPV) cells, a semiconductor is required that have a low band-gap, enable improved light harvesting by the photoactive layer and can lead to higher cell efficiencies.

Further requirements for the semiconductor are a good processability, especially for large-scale production of thin layers and desired patterns, and high stability, film uniformity and integrity of the organic semiconductor layer.

In prior art conjugated polymers based upon the benzo[1,2-b:4,5-b']dithiophene were reported for example in U.S. Pat. No. 7,524,922 B2. Primarily, the disclosed benzo[1,2-b:4,5-b']dithiophene polymers were to be used as an organic semiconductor in transistor applications. However, specific co-polymer variations are attractive candidates for photovoltaic applications, specifically in BHJ OPV devices.

By the incorporation of the electron-donating benzo[1,2-b:4,5-b']dithiophene unit and an electron-accepting unit into a co-polymer i.e. a "donor-acceptor" polymer, a reduction of the bandgap can be achieved, which enables improved light harvesting properties BHJ OPV devices. For example, Yang and co-workers have reported co-polymers of 4,8-dialkoxybenzo[1,2-b:4,5-b']dithiophene with various electron-accepting units to yield optical bandgaps of 1.05-1.70 eV.[see J. Hou, M.-H. Park, S. Zhang, Y. Yao, L.-M. Chen, J.-H. Li and Y. Yang, *Macromolecules*, 2008, 41, 6012]. In comparison, they reported the homopolymer of 4,8-dialkoxybenzo[1,2-b:4,5-b']dithiophene to have an optical bandgap of 2.13 eV. Further reports of co-polymers of 4,8-dialkoxybenzo[1,2-b:4,5-b']dithiophene with thieno[3,4-b]thiophene carboxylate and thieno[3,4-b]thiophene ketone units respectively have been made and are summarized in Table 1 [see Y. Liang, Y. Wu, D. Feng, S.-T. Tsai, H.-J. Son, G. Li and L. Yu, *J. Am. Chem. Soc.*, 2009, 131, 56 and J. Hou, H.-Y. Chen, S. Zhang, R. I. Chen, Y. Yang, Y. Wu and G. Li, *J. Am. Chem. Soc.*, 2009, 131, 15586]. An additional report of a co-polymer of 4,8-dialkylbenzo[1,2-b:4,5-b']dithiophene with a thieno[3,4-b]thiophene carboxylate unit has been made and is also summarized in Table 1 [see Y. Liang, D. Feng, Y. Wu, S.-T. Tsai, G. Li, C. Ray and L. Yu, *J. Am. Chem. Soc.*, 2009, 131, 7792].

By the expansion of the electron-donating 4,8-dialkylbenzo[1,2-b:4,5-b']dithiophene unit with the addition of two 3-alkylthiophene units to yield the novel 2,6-bis(3-alkyl-2-thienyl)-4,8-dialkylbenzo[1,2-b:4,5-b']dithiophene unit, the copolymer's solubility and electronic properties can be further modified. Meanwhile, Ong and co-workers have claimed the application in transistor devices of the homopolymer, poly[2,6-bis(3-alkyl-2-thienyl)-4,8-dialkylbenzo[1,2-b:4,5-b']dithiophene] [see EP 1 916 250 A1], but there are no reports of "donor-acceptor" co-polymers incorporating this unit nor their application in BHJ photovoltaic devices.

US 2010/0078074 A1 discloses a polymer comprising repeat units of the following formula as active material for photoelectric devices:

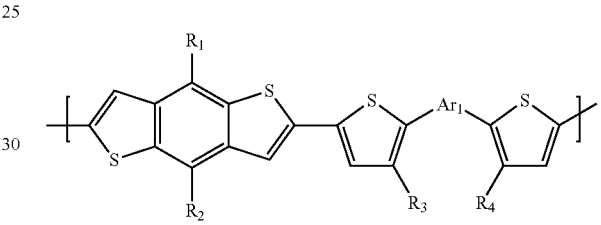

wherein R1, R2, R3 and R4 are alkyl or alkoxy groups with 1 to 18 C atoms, and Ar1 is a mono-, bi- or polycyclic N-containing heteroarylene with 1 to 5 N atoms. However, the alkyl substituents R3 and R4 at the thiophene rings pointing towards the heteroarylene group Ar1 can cause problems, especially in case R3 and R4 are longer alkyl chains and Ar1 is a bulky group that contains e.g. a benzene ring, due to steric hindrance which disturbs the planar structure of the polymer that is desired for good charge transport properties.

WO 2010/135701 A1 discloses random copolymers of first and second monomeric units, each comprising one benzodithiophene, one benzothidiazole and two thiophene rings, wherein in the first monomeric unit all thiophene rings are unsubstituted and in the second monomeric unit all thiophene rings are substituted, however, it does not disclose polymers as claimed in the present invention.

Therefore, there is still a need for OSC materials that do not have the drawbacks of prior art materials and are suitable for use in OFET and BHJ OPV devices.

The materials should be easy to synthesize, show good structural organization and film-forming properties, exhibit good electronic properties, especially a high charge carrier mobility, good processibilty, especially a high solubility in organic solvents, and high stability in air. For use in OPV cells, they should have a low band-gap, which enable improved light harvesting by the photoactive layer and can lead to higher cell efficiencies. For use in OFETs there is also a need for OSC materials that allow improved charge injection into the semiconducting layer from the source-drain electrodes.

It was an aim of the present invention to provide improved polymers for use as OSC materials especially in BHJ OPV devices, but also in OFET devices, which show the above-mentioned advantageous properties, and which do not show the above-mentioned disadvantages of prior art materials. Another aim of the invention was to extend the pool of OSC materials available to the expert. Other aims of the present invention are immediately evident to the expert from the following detailed description.

The inventors of the present invention have found that these aims can be achieved by providing the polymers as described hereinafter, which comprise benzodithiophene units as electron-donating units, thiophene units, and optionally comprise electron-accepting units like for example benzothioadiazole.

SUMMARY OF THE INVENTION

The invention relates to conjugated polymers of formula I:

$$*-[-(A)_i-((B)_k-(Ar)_o)_m]_n-*$$ I wherein
A is on each occurrence identically or differently a group selected from the following formulae IIa
IIb
IIc
IId
IIe B is on each occurrence identically or differently a group selected from the following formulae IIf
IIg
IIh
IIi
IIk
IIm
IIn $X^1$ and $X^2$ are, on each occurrence identically or differently, and independently of each other, O, S or Se, $R^1$ and $R^2$ are, on each occurrence identically or differently, and independently of each other, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or an aryl, heteroaryl, aryloxy or heteroaryloxy group having 2 to 40 ring atoms that is unsubstituted or substituted by one or more non-aromatic groups $R^5$, $R^3$ and $R^4$ on each occurrence identically or differently, and independently of each other, denote H or have one of the meanings given for $R^1$, $R^0$ and $R^{00}$ are independently of each other H or an optionally substituted carbyl or hydrocarbyl group optionally comprising one or more hetero atoms, Ar is, on each occurrence identically or differently, an aryl or heteroaryl group that is optionally substituted by one or more groups $R^1$, $R^5$ is, on each occurrence identically or differently, H, halogen, —CN, —NC, —NCO, —NCS, —OCN, —SCN, —C(=O)NR$^0$R$^{00}$, —C(=O)X$^0$, —C(=O)R$^0$, —NH$_2$, —NR$^0$R$^{00}$, —SH, —SR$^0$, —SO$_3$H, —SO$_2$R$^0$, —OH, —NO$_2$, —CF$_3$, —SF$_5$, optionally substituted silyl, carbyl or hydrocarbyl with 1 to 40 C atoms that is optionally substituted and optionally comprises one or more hetero atoms, or P-Sp-, P is a polymerisable group, Sp is a spacer group or a single bond, $X^0$ is halogen, m is on each occurrence identically or differently 0 or 1, wherein in at least one repeating unit m is 1, o is on each occurrence identically or differently 0 or 1, wherein in at least one repeating unit o is 1, i and k are, on each occurrence identically or differently, and independently of each other, 0 or 1, wherein in at least one repeating unit at least one of i and k is 1, n is an integer >1.

The invention further relates to a polymer blend comprising one or more polymers according to the present invention and one or more polymers, preferably selected from polymers having semiconducting, charge transport, hole/electron transport, hole/electron blocking, electrically conducting, photoconducting or light emitting properties.

The invention further relates to a formulation comprising one or more polymers or polymer blends according to the present invention and one or more solvents, preferably selected from organic solvents.

The invention further relates to the use of polymers, polymer blends and formulations according to the present invention as charge transport, semiconducting, electrically conducting, photoconducting or light emitting material in optical, electrooptical, electronic, electroluminescent or photoluminescent components or devices.

The invention further relates to a charge transport, semiconducting, electrically conducting, photoconducting or light emitting material or component comprising one or more polymers, polymer blends of formulations according to the present invention.

The invention further relates to an optical, electrooptical or electronic component or device comprising one or more polymers, polymer blends, formulations, components or materials according to the present invention.

The optical, electrooptical, electronic electroluminescent and photoluminescent components or devices include, without limitation, organic field effect transistors (OFET), thin film transistors (TFT), integrated circuits (IC), logic circuits, capacitors, radio frequency identification (RFID) tags, devices or components, organic light emitting diodes (OLED), organic light emitting transistors (OLET), flat panel displays, backlights of displays, organic photovoltaic devices (OPV), bulk heterojunction (BHJ) OPV devices, solar cells, laser diodes, photoconductors, photodetectors, electrophotographic devices, electrophotographic recording devices, organic memory devices, sensor devices, charge injection layers, charge transport layers or interlayers in polymer light emitting diodes (PLEDs), organic plasmon-emitting diodes (OPEDs), Schottky diodes, planarising layers, antistatic films, polymer electrolyte membranes (PEM), conducting substrates, conducting patterns, electrode materials in batteries, alignment layers, biosensors, biochips, security markings, security devices, and components or devices for detecting and discriminating DNA sequences.

DETAILED DESCRIPTION OF THE INVENTION

The term "polymer" generally means a molecule of high relative molecular mass, the structure of which essentially comprises the multiple repetition of units derived, actually or conceptually, from molecules of low relative molecular mass (PAC, 1996, 68, 2291). The term "oligomer" generally means a molecule of intermediate relative molecular mass, the structure of which essentially comprises a small plurality of units derived, actually or conceptually, from molecules of lower relative molecular mass (PAC, 1996, 68, 2291). In a preferred sense according to the present invention a polymer means a compound having >1, preferably ≥5 repeating units, and an oligomer means a compound with >1 and <10, preferably <5, repeating units.

Above and below, in a formula showing a polymer, like formula I and its subformulae, an asterisk ("*") denotes a linkage to the adjacent repeating unit in the polymer chain.

The terms "repeating unit" and "monomeric unit" mean the constitutional repeating unit (CRU), which is the smallest constitutional unit the repetition of which constitutes a regular macromolecule, a regular oligomer molecule, a regular block or a regular chain (PAC, 1996, 68, 2291).

The polymers of the present invention contain at least one repeating unit wherein m is 1, and do further contain at least one repeating unit wherein o is 1 and which can be the same repeating unit as the aforementioned or a different repeating unit, and do further contain contain at least one repeating unit wherein i and/or k is 1 and which can be the same repeating unit as be aforementioned or a different repeating unit.

The term "leaving group" means an atom or group (charged or uncharged) that becomes detached from an atom in what is considered to be the residual or main part of the molecule taking part in a specified reaction (see also PAC, 1994, 66, 1134).

The term "conjugated" means a compound containing mainly C atoms with $sp^2$-hybridisation (or optionally also sp-hybridisation), which may also be replaced by hetero atoms. In the simplest case this is for example a compound with alternating C—C single and double (or triple) bonds, but does also include compounds with units like 1,3-phenylene. "Mainly" means in this connection that a compound with naturally (spontaneously) occurring defects, which may lead to interruption of the conjugation, is still regarded as a conjugated compound.

Unless stated otherwise, the molecular weight is given as the number average molecular weight $M_n$ or weight average molecular weight $M_w$, which is determined by gel permeation chromatography (GPC) against polystyrene standards in eluent solvents such as tetrahydrofuran, trichloromethane (TCM, chloroform), chlorobenzene or 1,2,4-trichlorobenzene. Unless stated otherwise, trichloromethane is used as solvent. The degree of polymerization (n) means the number average degree of polymerization given as $n=M_n/M_U$, wherein $M_U$ is the molecular weight of the single repeating unit as described in J. M. G. Cowie, *Polymers: Chemistry & Physics of Modern Materials*, Blackie, Glasgow, 1991.

The term "carbyl group" as used above and below denotes any monovalent or multivalent organic radical moiety which comprises at least one carbon atom either without any non-carbon atoms (like for example —C≡C—), or optionally combined with at least one non-carbon atom such as N, O, S, P, Si, Se, As, Te or Ge (for example carbonyl etc.). The term "hydrocarbyl group" denotes a carbyl group that does additionally contain one or more H atoms and optionally contains one or more hetero atoms like for example N, O, S, P, Si, Se, As, Te or Ge.

A carbyl or hydrocarbyl group comprising a chain of 3 or more C atoms may also be straight-chain, branched and/or cyclic, including spiro and/or fused rings.

Preferred carbyl and hydrocarbyl groups include alkyl, alkoxy, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from N, O, S, P, Si, Se, As, Te and Ge.

The carbyl or hydrocarbyl group may be a saturated or unsaturated acyclic group, or a saturated or unsaturated cyclic group. Unsaturated acyclic or cyclic groups are preferred, especially aryl, alkenyl and alkynyl groups (especially ethynyl). Where the $C_1$-$C_{40}$ carbyl or hydrocarbyl group is acyclic, the group may be straight-chain or branched. The $C_1$-$C_{40}$ carbyl or hydrocarbyl group includes for example: a $C_1$-$C_{40}$ alkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_6$-$C_{12}$ aryl group and a $C_4$-$C_{20}$ polyenyl group, respectively. Also included are combinations of groups having carbon atoms and groups having hetero atoms, like e.g. an alkynyl group, preferably ethynyl, that is substituted with a silyl group, preferably a trialkylsilyl group.

Aryl and heteroaryl preferably denote a mono-, bi-or tricyclic aromatic or heteroaromatic group with up to 25 C atoms that may also comprise condensed rings and is optionally substituted with one or more groups L as defined above, and wherein one or more carbon atoms are optionally substituted by a heteroatom, which is preferably selected from N, P, As, O, S, Se and Te.

Very preferred substituents L are selected from halogen, most preferably F, or alkyl, alkoxy, oxaalkyl, thioalkyl, fluoroalkyl and fluoroalkoxy with 1 to 12 C atoms or alkenyl, alkynyl with 2 to 12 C atoms.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

In another preferred embodiment of the present invention, $R^1$ and/or $R^2$ is selected from primary, secondary or tertiary alkyl or alkoxy with 1 to 30 C atoms, wherein one or more H atoms are optionally replaced by F, or aryl, alkylated aryl or alkoxy aryl with 4 to 40 C atoms. Especially preferred groups $R^1$ and $R^2$ of this type are selected from the group consisting of the following formulae

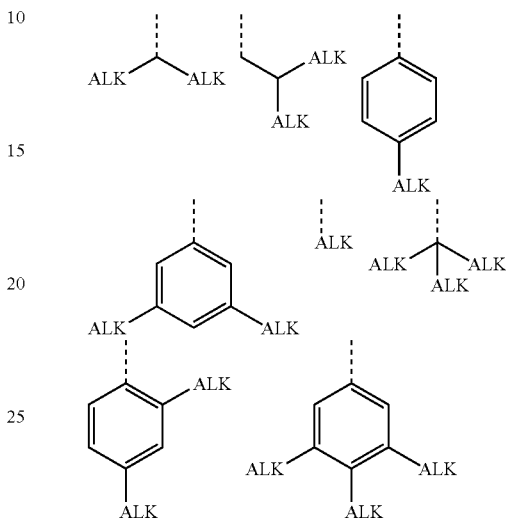

wherein "ALK" denotes optionally fluorinated, preferably linear, alkyl with 1 to 20, preferably 1 to 12 C-atoms, in case of tertiary alkyl very preferably 1 to 9 C atoms, and the dashed line denotes the link to the N-atom of the phenanthrocarbazole core in formula I. Especially preferred among these groups are those wherein all ALK subgroups are identical.

An alkenyl group, wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example. Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-,7-, 8- or 9-oxadecyl, for example.

In an alkyl group wherein one $CH_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e where one $CH_2$ group is replaced by —S—, is preferably straight-chain thiomethyl (—$SCH_3$), 1-thioethyl (—$SCH_2CH_3$), 1-thiopropyl (=—$SCH_2CH_2CH_3$), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the $CH_2$ group adjacent to the $sp^2$ hybridised vinyl carbon atom is replaced.

A fluoroalkyl group is preferably straight-chain perfluoroalkyl $C_tF_{2t+1}$, wherein t is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$.

The above-mentioned alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethyl-hexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxy-carbonyl, 2-methylbutyryloxy, 3-methylvaleroyloxy, 4-methylhexanoyloxy, 2-chloropropionyloxy, 2-chloro-3-methylbutyryloxy, 2-chloro-4-methyl-valeryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

—$CY^1$=$CY^2$— is preferably —CH=CH—, —CF=CF— or —CH=C(CN)—.

Halogen is F, Cl, Br or I, preferably F, Cl or Br.

The polymers may also be substituted with a polymerisable or reactive group, which is optionally protected during the process of forming the polymer. Particular preferred polymers of this type are those of formula I wherein $R^1$ denotes P-Sp. These polymers are particularly useful as semiconductors or charge transport materials, as they can be crosslinked via the groups P, for example by polymerisation in situ, during or after processing the polymer into a thin film for a semiconductor component, to yield crosslinked polymer films with high charge carrier mobility and high thermal, mechanical and chemical stability.

Preferably the polymerisable or reactive group P is selected from $CH_2$=$CW^1$—CO—O—, $CH_2$=$CW^1$—CO—,

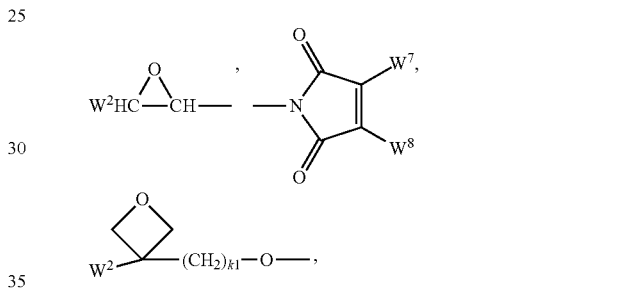

$CH_2$=$CW^2$—(O)$_{k1}$—, $CW^1$=CH—CO—(O)$_{k3}$—, $CW^1$=CH—CO—NH—, $CH_2$=$CW^1$—CO—NH—, $CH_3$—CH=CH—O—, ($CH_2$=CH)$_2$CH—OCO—, ($CH_2$=CH—$CH_2$)$_2$CH—O—CO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—, HS—$CW^2W^3$—, $HW^2$N—, HO—$CW^2W^3$—N$_H$—, $CH_2$=$C_H$—(CO—O)$_{k1}$-Phe-(O)$_{k2}$—, $CH_2$=CH—(O)$_{k1}$-Phe-(O)$_{k2}$—, Phe-CH=CH—, HOOC—, OCN—, and $W^4W^5W^6$Si—, with $W^1$ being H, F, Cl, CN, $CF_3$, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently d of each other Cl, oxaalkyl or oxacarbonylalkyl with 1 to 5 C-atoms, $W^7$ and $W^8$ being independently of each other H, Cl or alkyl with 1 to 5 C-atoms, Phe being 1,4-phenylene that is optionally substituted by one or more groups L as defined above, $k_1$, $k_2$ and $k_3$ being independently of each other 0 or 1, $k_3$ preferably being 1, and $k_4$ being an integer from 1 to 10.

Alternatively P is a protected derivative of these groups which is non-reactive under the conditions described for the process according to the present invention. Suitable protective groups are known to the ordinary expert and described in the literature, for example in Green, "Protective Groups in Organic Synthesis", John Wiley and Sons, New York (1981), like for example acetals or ketals.

Especially preferred groups P are $CH_2$=CH—CO—O—, $CH_2$=C($CH_3$)—CO—O—, $CH_2$=CF—CO—O—, $CH_2$=CH—O—, ($CH_2$=CH)$_2$CH—O—CO—, ($CH_2$=CH)$_2$CH—O—,

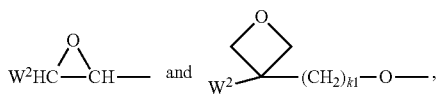

or protected derivatives thereof. Further preferred groups P are selected from the group consisting of vinyloxy, acrylate, methacrylate, fluoroacrylate, chloracrylate, oxetan and epoxy groups, very preferably an acrylate or methacrylate group.

Polymerisation of group P can be carried out according to methods that are known to the ordinary expert and described in the literature, for example in D. J. Broer; G. Challa; G. N. Mol, *Macromol. Chem,* 1991, 192, 59.

The term "spacer group" is known in prior art and suitable spacer groups Sp are known to the ordinary expert (see e.g. Pure Appl. Chem. 73(5), 888 (2001). The spacer group Sp is preferably of formula Sp'-X', such that P-Sp- is P-Sp'-X'—, wherein Sp' is alkylene with up to 30 C atoms which is unsubstituted or mono- or polysubstituted by F, Cl, Br, I or CN, it being also possible for one or more non-adjacent CH$_2$ groups to be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that O and/or S atoms are not linked directly to one another, X' is —O—, —S—, —CO—, —COO—, —OCO—, —O—COO—, —CO—NR$^0$—, —NR$^0$—CO—, —NR$^0$—CO—NR$^{00}$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, R$^0$ and R$^{00}$ are independently of each other H or alkyl with 1 to 12 C-atoms, and Y$^1$ and Y$^2$ are independently of each other H, F, Cl or CN.

X' is preferably —O—, —S—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C— or a single bond, in particular —O—, —S—, —C≡C—, —CY$^1$=CY$^2$— or a single bond. In another preferred embodiment X' is a group that is able to form a conjugated system, such as —C≡C— or —CY$^1$=CY$^2$—, or a single bond.

Typical groups Sp' are, for example, —(CH$_2$)$_p$—, —(CH$_2$CH$_2$O)$_q$—CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$—O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

The polymers of formula I can be synthesized in a regioregular and regioselective fashion via chemical polymerization. They are easy to synthesize and exhibit several advantageous properties, like a low bandgap, a high charge carrier mobility, a high solubility in organic solvents, a good processability for the device manufacture process, a high oxidative stability and a long lifetime in electronic devices.

Especially preferred are polymers of formula Ia

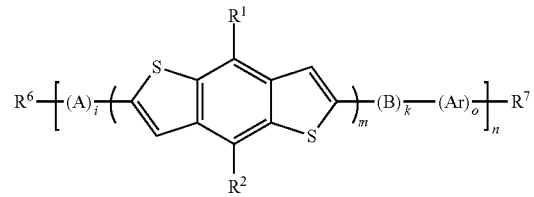

Ia wherein R$^{1-4}$, Ar, i, k, m, n and o have the meanings of formula I, and R$^6$ and R$^7$ have independently of each other one of the meanings of R$^3$ of formula I or its preferred meanings as given above and below, and are preferably selected from H or halogen, —CH$_2$Cl, —CHO, —CH=CH$_2$, —SiR'R''R''', —SnR'R''R''', —BR'R'', —B(OR')(OR''), —B(OH)$_2$, or P-Sp, wherein P and Sp are as defined above, and R', R'' and R''' have independently of each other one of the meanings of R$^0$ given above and R' and R'' may also form a ring together with the hetero atom to which they are attached.

In the polymers according to the the present invention, the total number of repeating units n is preferably ≥5, very preferably ≥10, most preferably ≥50, and preferably up to 500, very preferably up to 1,000, most preferably up to 2,000, including any combination of the aforementioned lower and upper limits of n.

The polymers of the present invention include homopolymers, statistical copolymers, random copolymers, alternating copolymers and block copolymers, and combinations of the aforementioned. The polymers of the present invention are formed by identical or different repeating units of formula III

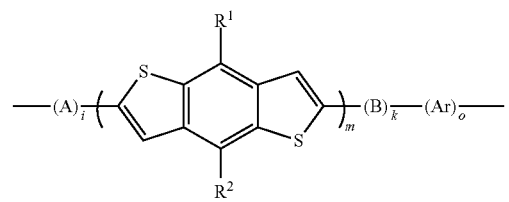

III wherein R$^{1-2}$, A, B, Ar, i, k, m and o have the meanings given in formula I.

Another aspect of the invention relates to monomers of formula IIIa

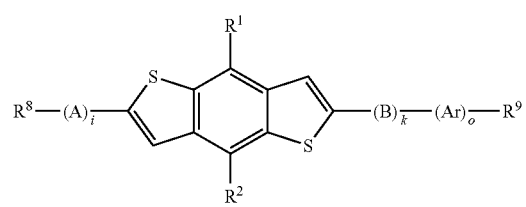

IIIa wherein $R^1$, $R^2$, A, B and Ar have the meanings given in formula Ia, i, k and o are independently of each other 0 or 1, with at least one of i, k and o being 1, and $R^8$ and $R^9$ are identical or different groups having one of the meanings of $R^6$ in formula Ia different from H or being selected from the group consisting of Cl, Br, I, O-tosylate, O-triflate, O-mesylate, O-nonaflate, —SiMe$_2$F, —SiMeF$_2$, —O—SO$_2$Z$^1$, —B(OZ$^2$)$_2$, —CZ$^3$=C(Z$^3$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group.

Preferably the polymers of formula I and Ia, the repeating units of formula III and the monomers of formula IIIa are selected from the following list of preferred embodiments or any combinations thereof:

if i=m=k=o=1, A is of formula IIa and B is of formula IIg, then all groups $R^4$ are H or all groups $R^4$ are different from H,
  if i=m=k=o=1, A is of formula IIa, B is of formula IIg, and Ar is an optionally substituted benzofused heteroaryl moiety comprising 1-6 hetero atoms, then all groups $R^4$ are H or all groups $R^4$ are different from H,
  if i=m=k=o=1, A is of formula IIa, B is of formula IIg, and Ar is benzo[2,1,3]thiadiazole-4,7-diyl that is optionally substituted in 5- and 6-position with $C_{1-40}$ alkyl groups, then all groups $R^4$ are H or all groups $R^4$ are different from H,
  m is 1 and o is 1,
  i is 1 and k is 1,
  i is 1 and k is 0,
  k is 1 and i is 0,
  A is of formula IIa and B is of formula IIg,
  A is of formula IIb and B is of formula IIh,
  A is of formula IIc and B is of formula IIi,
  A is of formula IId and B is of formula IIk,
  A is of formula IIe and B is of formula IIm,
  A is of formula IIf and B is of formula IIn,
  A is of formula IId, IIe or IIf, and $X^1$ and $X^2$ are S,
  B is of formula IIk, IIm or IIn, and X' and $X^2$ are S,
  A is of formula IId, IIe or IIf, and X' and $X^2$ are Se,
  B is of formula IIk, IIm or IIn, and X' and $X^2$ are Se,
  A is of formula IIb, IIc, IId, IIe or IIf wherein $R^3$ is H,
  B is of formula IIh, IIi, IIk, IIm or IIn wherein $R^3$ is H,
  the polymer contains, preferably consists of, repeating units of formula III wherein i=m=1 and k=o=0 and repeating units of formula III wherein i=m=0 and k=o=1,
  the polymer is a random copolymer formed by identical repeating units of formula III wherein i=m=1 and k=o=0 and identical repeating units of formula III wherein i=m=0 and k=o=1,
  the polymer contains, preferably consists of, repeating units of formula III wherein i=m=k=o=1,
  the polymer is formed by identical repeating units of formula III wherein i=m=k=o=1,
  n is at least 5, preferably at least 10, very preferably at least 50, and up to 2,000, preferably up to 500.
  Mw is at least 5,000, preferably at least 8,000, very preferably at least 10,000, and preferably up to 300,000, very preferably up to 100,000,
  in formula IIa, $R^4$ is H,
  in formula IIg, $R^4$ is H,
  in group A, $R^3$ is H and at least one $R^4$ is different from H,
  in group B, $R^3$ is H and at least one $R^4$ is different from H,
  in group A and/or B, $R^3$ is H and $R^4$ is H,
  in group A and/or B, $R^3$ and $R^4$ are different from H,
  $R^1$ and/or $R^2$ denote straight-chain alkyl, alkoxy or thioalkyl with 1 to 30, preferably 5 to 15 C atoms, wherein one or more H atoms are optionally replaced by F,
  $R^1$ and/or $R^2$ denote branched alkyl, alkoxy or thioalkyl with 3 to 30, preferably 5 to 15 C atoms, wherein one or more H atoms are optionally replaced by F,
  $R^1$ and/or $R^2$ denote primary alkyl, alkoxy or thioalkyl with 1 to 30 C atoms, wherein one or more H atoms are optionally replaced by F,
  $R^1$ and/or $R^2$ denote secondary alkyl, alkoxy or thioalkyl with 3 to 30 C atoms, or tertiary alkyl, alkoxy or thioalkyl with 4 to 30 C atoms, wherein in all these groups one or more H atoms are optionally replaced by F,
  $R^1$ and/or $R^2$ are aryl, alkylated aryl or alkoxy aryl with 4 to 40 C atoms,
  $R^y$ and/or $R^2$ are —CO—$R^y$, —CO—O—$R^y$, or —O—CO—$R^y$, very preferably —CO—$R^y$ or —CO—O—$R^y$, wherein $R^y$ is straight-chain, branched or cyclic alkyl with 1 to 30 C atoms, in which one or more non-adjacent C atoms are optionally replaced by —O—, —S—, —CO—, —CO—O—, —O—CO—, —O—CO—O—, —CR$^0$=CR$^{00}$— or —C≡C— and in which one or more H atoms are optionally replaced by F, Cl, Br, I or CN, or $R^y$ is aryl or heteroaryl having 2 to 30 C atoms that is unsubstituted or substituted by one or more non-aromatic groups $R^5$ as defined in formula I,
  $R^3$ and/or $R^4$, when being different from H, denote straight-chain alkyl, alkoxy or thioalkyl with 1 to 15 C atoms, wherein one or more H atoms are optionally replaced by F,
  $R^3$ and/or $R^4$, when being different from H, denote branched alkyl, alkoxy or thioalkyl with 3 to 15 C atoms, wherein one or more H atoms are optionally replaced by F,
  $R^3$ and/or $R^4$, when being different from H, denote primary alkyl, alkoxy or thiolakyl with 1 to 30 C atoms, wherein one or more H atoms are optionally replaced by F,
  $R^3$ and/or $R^4$, when being different from H, denote secondary alkyl, alkoxy or thioalkyl with 3 to 30 C atoms, or tertiary alkyl, alkoxy or thioalkyl with 4 to 30 C atoms, wherein in all these groups one or more H atoms are optionally replaced by F,
  $R^3$ and/or $R^4$, when being different from H, denote aryl, alkylated aryl or alkoxy aryl with 4 to 40 C atoms,
  $R^3$ and/or $R^4$, when being different from H, denote —CO—$R^y$, —CO—O—$R^y$, or —O—CO—$R^y$, very preferably —CO—$R^y$ or —CO—O—$R^y$, wherein $R^y$ is straight-chain, branched or cyclic alkyl with 1 to 30 C atoms, in which one or more non-adjacent C atoms are optionally replaced by —O—, —S—, —CO—, —CO—O—, —O—CO—, —O—CO—O—, —CR$^0$=CR$^{00}$— or —C≡C— and in which one or more H atoms are optionally replaced by F, Cl, Br, I or CN, or $R^y$ is aryl or heteroaryl having 2 to 30 C atoms that is unsubstituted or substituted by one or more non-aromatic groups $R^5$ as defined in formula I,
  $R^y$ is primary alkyl with 1 to 30 C atoms, very preferably with 1 to 15 C atoms, secondary alkyl with 3 to 30 C atoms, or tertiary alkyl with 4 to 30 C atoms, wherein in all these groups one or more H atoms are optionally replaced by F,
  $R^y$ is —(CH$_2$)$_h$—CR$^a$R$^b$R$^c$, wherein h is 0, 1, 2, 3, 4 or 5, very preferably 0, 1 or 2, and $R^a$, $R^b$ and $R^c$ are independently of each other $C_1$-$C_{12}$-alkyl, very preferably $C_1$-$C_8$-alkyl, which is optionally substituted by one or more F atoms, and wherein optionally one of $R^a$, $R^b$ and $R^c$ is H, $R^y$ is aryl or alkylated aryl with 4 to 30 C atoms, $R^0$ and $R^{00}$ are selected from H or $C_1$-$C_{10}$-alkyl, $R^6$ and $R^7$ are selected from H, halogen, —CH$_2$Cl, —CHO, —CH=CH$_2$—SiR'R"R'", —SnR'R"R'", —BR'R", —B(OR')(OR"), —B(OH)$_2$, P-Sp, $C_1$-$C_{20}$-alkyl, $C_1$-$C_{20}$-alkoxy, $C_2$-$C_{20}$-alkenyl, $C_1$-$C_{20}$-fluoroalkyl and optionally substituted aryl or heteroaryl, $R^8$ and $R^9$ are, preferably independently of each other, selected from the group consisting of Cl, Br, I, O-tosylate, O-triflate, O-mesylate, O-nonaflate, —SiMe$_2$F, —SiMeF$_2$, —O—SO$_2$Z', —B(OZ$^2$)$_2$, —CZ$^3$=C(Z$^4$)$_2$, —C≡CH and —Sn(Z$^4$)$_3$, wherein $Z^{1-4}$ are selected from the group consisting of alkyl and aryl, each being optionally substituted, and two groups $Z^2$ may also form a cyclic group, Ar is substituted by one or more groups $R^1$, Ar is an aryl or heteroaryl group which has electron donor properties, including but not limited to aryl and heteroaryl groups selected from the group consisting of selenophene-2,5-diyl, thiophene-2,5-diyl, thieno[3,2-b]thiophene-2,5-diyl, thieno[2,3-b]thiophene-2,5-diyl, selenopheno[3,2-b]selenophene-2,5-diyl, selenopheno[2,3-b]selenophene-2,5-diyl, selenopheno[3,2-b]thiophene-2,5-diyl, selenopheno[2,3-b]thiophene-2,5-diyl, benzo[1,2-b:4,5-b']dithiophene-2,6-diyl, 2,2-dithiophene, 2,2-diselenophene, dithieno[3,2-b:2',3'-d]silole-5,5-diyl, 4H-cyclopenta[2,1-b:3,4-b']dithiophene-2,6-diyl, 2,7-di-thien-2-yl-carbazole, 2,7-di-thien-2-yl-fluorene, indaceno[1,2-b:5,6-b']dithiophene-2,7-diyl, benzo[1",2":4,5;4",5":4',5']bis(silolo[3,2-b:3',2'-b']thiophene)-2,7-diyl, 2,7-di-thien-2-yl-indaceno[1,2-b:5,6-b']dithiophene, 2,7-di-thien-2-yl-benzo[1",2":4,5;4",5":4',5']bis(silolo[3,2-b:3',2'-b']thiophene)-2,7-diyl, 2,7-di-thien-2-yl-phenanthro[1,10,9,8-c,d,e,f,g]carbazole, all of which are unsubstituted, or mono- or polysubstituted, preferably with $R^1$ as defined above and below, Ar is an aryl or heteroaryl group which has electron acceptor properties, including but not limited to aryl and heteroaryl groups selected from the group consisting of benzo[2,1,3]thiadiazole-4,7-diyl, 5,6-dialkyl-benzo[2,1,3]thiadiazole-4,7-diyl, 5,6-dialkoxybenzo[2,1,3]thiadiazole-4,7-diyl, benzo[2,1,3]selenadiazole-4,7-diyl, 5,6-dialkoxy-benzo[2,1,3]selenadiazole-4,7-diyl, benzo[1,2,5]thiadiazole-4,7-diyl, benzo[1,2,5]selenadiazole-4,7-diyl, benzo[2,1,3]oxadiazole-4,7-diyl, 5,6-dialkoxybenzo[2,1,3]oxadiazole-4,7-diyl, 2H-benzotriazole-4,7-diyl, 2,3-dicyano-1,4-phenylene, 2,5-dicyano,1,4-phenylene, 2,3-difluro-1,4-phenylene, 2,5-difluoro-1,4-phenylene, 2,3,5,6-tetrafluoro-1,4-phenylene, 3,4-difluorothiophene-2,5-diyl, thieno[3,4-b]pyrazine-2,5-diyl, quinoxaline-5,8-diyl, thieno[3,4-b]thiophene-4,6-diyl, thieno[3,4-b]thiophene-6,4-diyl, 3,6-pyrrolo[3,4-c]pyrrole-1,4-dione, all of which are unsubstituted, or mono- or polysubstituted, preferably with $R^1$ as defined above and below, wherein "alkyl" means a straight-chain or branched alkyl group with 1 to 30 C atoms and "alkoxy" means a straight-chain or branched alkoxy group with 1 to 30 C atoms.

Preferred polymers of formula I are selected from the following formulae:

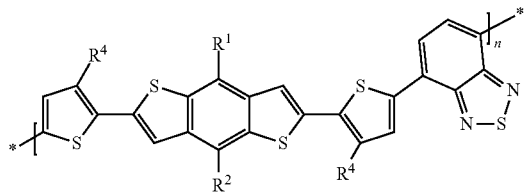

I1

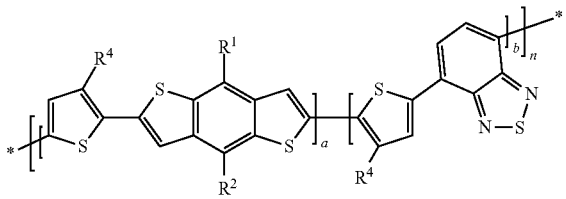

I2

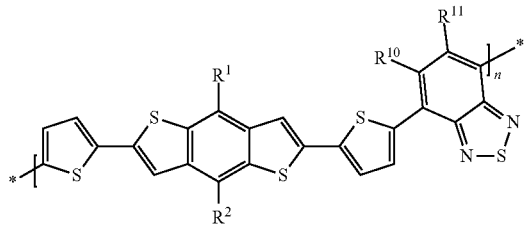

I3

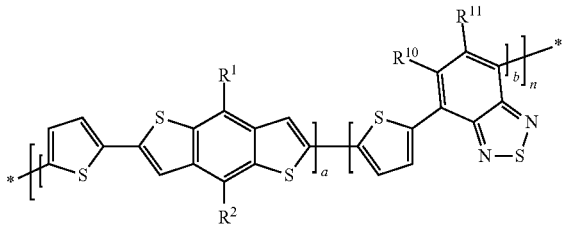

I4

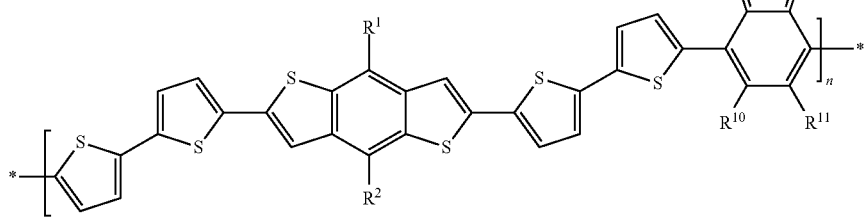

I5

-continued
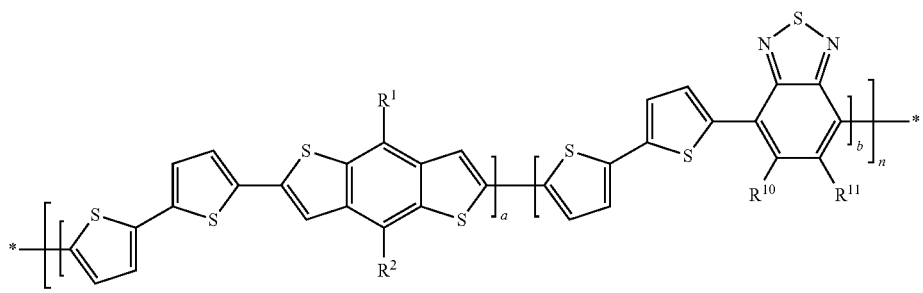
I6
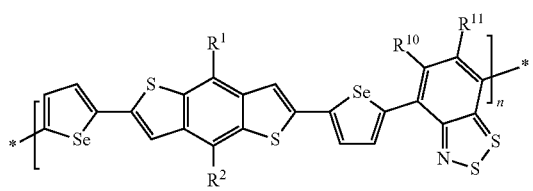
I7
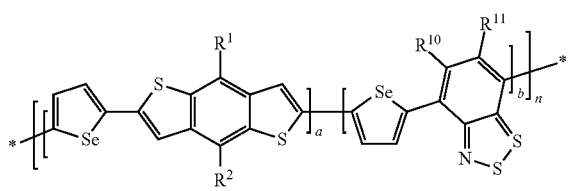
I8
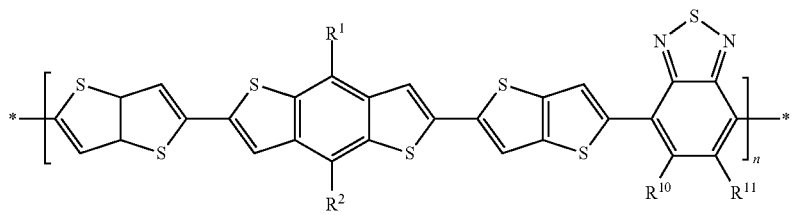
I9
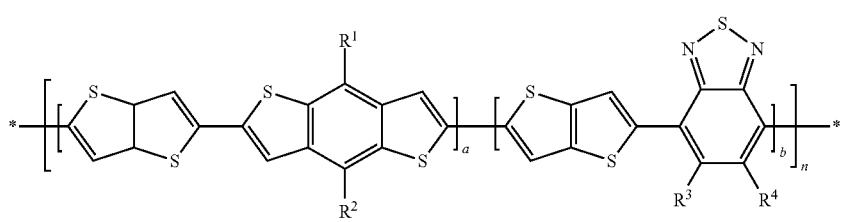
I10
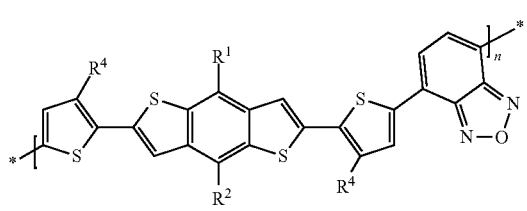
I11
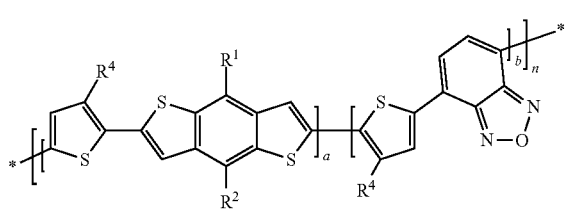
I12
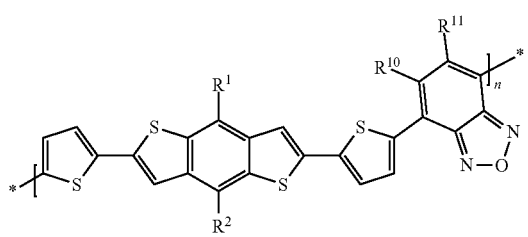
I13
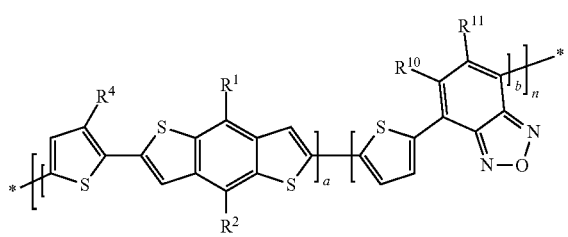
I14

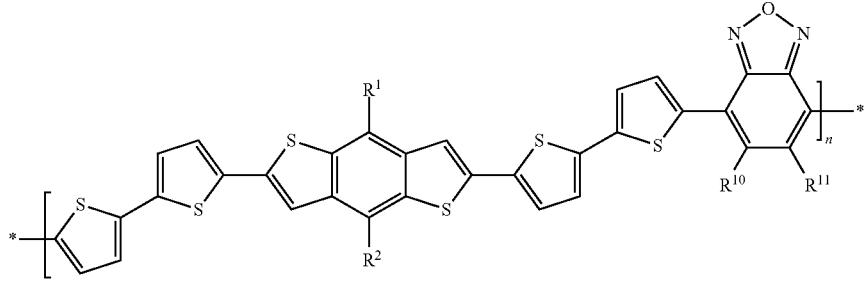

I15

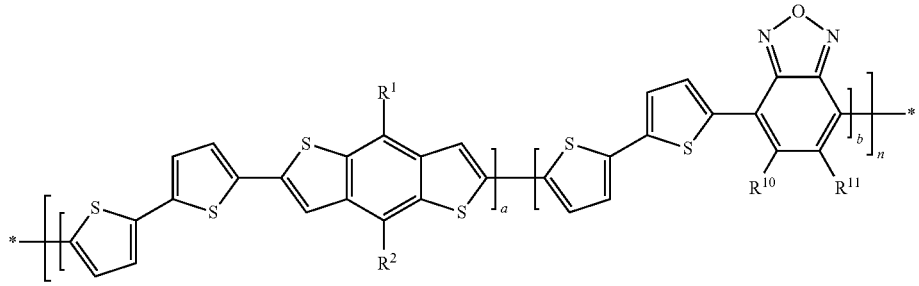

I16

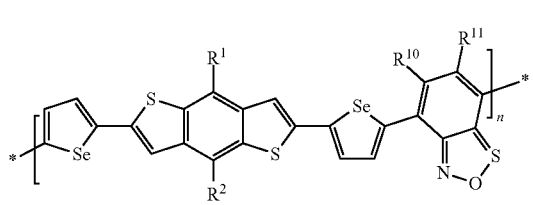 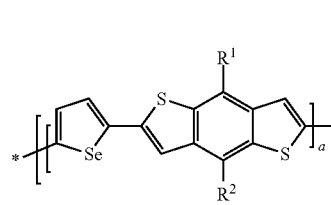

I17                              I18

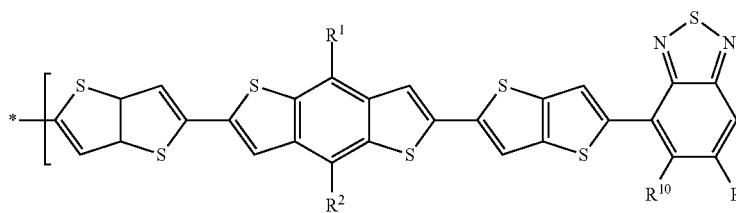

I19

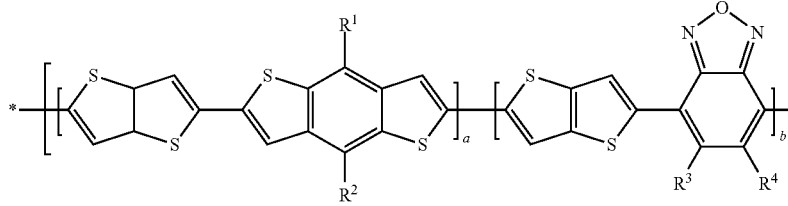

I20 wherein $R^1$, $R^2$, $R^4$ and n have the meanings given in formula I or of the preferred meanings given above, with $R^4$ being different from H, $R^{10}$ and $R^{11}$ have independently of each other one of the meanings of $R^1$ given in formula I or of the preferred meanings given above, and preferably have the same meaning, and wherein formula I2, I4, 6, I8, I10, I12, I14, I16, I18 and I20 denote random copolymers formed by units wherein a=1 and b=0 and units wherein a=0 and b=1.

Preferably $R^{10}$ and $R^{11}$ are selected from straight-chain or branched alkyl, alkoxy or thioalkyl with 1 to 30 C atoms, or ketone (—CO—$R^y$) or carboxylic acid ester (—CO—O—$R^y$), wherein $R^y$ is straight-chain, branched or cyclic alkyl with 1 to 30 C atoms, and wherein in all aforementioned groups one or more H atoms are optionally replaced by F.

Further preferably $R^{10}$ and $R^{11}$ are selected from straight-chain or branched alkoxy or thioalkyl with 1 to 30 C atoms, or ketone (—CO—$R^y$) or carboxylic acid ester (—CO—O—$R^y$), wherein $R^y$ is straight-chain, branched or cyclic alkyl with 1 to 30 C atoms, and wherein in all aforementioned groups one or more H atoms are optionally replaced by F.

In another preferred embodiment $R^{10}$ and $R^{11}$ are different from an ester group.

Preferred polymers of formula Ia are selected of the formula $R^6$-chain-$R^7$ wherein "chain" is a polymer chain of formula I1-I18, and $R^6$ and $R^7$ have the meanings given in formula Ia or one of the preferred meanings given above and below.

The polymers of the present invention can be synthesized according to or in analogy to methods that are known to the skilled person and are described in the literature. Other methods of preparation can be taken from the examples. For example, they can be suitably prepared by aryl-aryl coupling reactions, such as Yamamoto coupling, Suzuki coupling, Stille coupling, Sonogashira coupling, Heck coupling or Buchwald coupling. Suzuki coupling and Yamamoto coupling are especially preferred.

The monomers which are polymerised to form the polymers of formula I and Ia can be prepared according to methods which are known to the person skilled in the art.

Another aspect of the invention is a process for preparing a polymer, comprising the step of coupling one or more identical or different monomers of formula IIIa, wherein o is 0, and i and k are independently of each other 0 or 1, with one or more identical or different comonomers of the formula $R^8$—Ar—$R^9$ and optionally one or more identical or different comonomers selected from the following formulae $R^8$-A-$R^9$ $R^8$—B—$R^9$ wherein A, B and Ar are as defined in formula I and $R^8$ and $R^9$ are as defined in formula IIIa, in a polymerisation reaction, preferably in an aryl-aryl coupling reaction.

Preferred methods for polymerisation are those leading to C—C-coupling or C—N-coupling, like Suzuki polymerisation, as described for example in WO 00/53656, Yamamoto polymerisation, as described in for example in T. Yamamoto et al., Progress in Polymer Science 1993, 17, 1153-1205 or in WO 2004/022626 A1, and Stille coupling. For example, when synthesizing a linear polymer by Yamamoto polymerisation, monomers as described above having two reactive halide groups $R^{7,8}$ is preferably used. When synthesizing a linear polymer by Suzuki polymerisation, preferably a monomer as described above is used wherein at least one reactive group $R^{7,8}$ is a boronic acid or boronic acid derivative group.

Suzuki polymerisation may be used to prepare statistical, alternating and block random copolymers. The synthesis of statistical, alternating and block copolymers is described in detail for example in WO 03/048225 A2 or WO 2005/014688 A2.

Suzuki polymerisation employs a Pd(0) complex or a Pd(II) salt. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol)$_4$. Preferred Pd(II) salts include palladium acetate, i.e. Pd(OAc)$_2$. Suzuki polymerisation is performed in the presence of a base, for example sodium carbonate, potassium phosphate or an organic base such as tetraethylammonium carbonate. Yamamoto polymerisation employs a Ni(0) complex, for example bis(1,5-cyclooctadienyl) nickel(0).

As alternatives to halogens as described above, leaving groups of formula —O—SO$_2$Z$^1$ can be used wherein Z$^1$ is as described above. Particular examples of such leaving groups are tosylate, mesylate and triflate.

Especially suitable and preferred synthesis methods for the monomers are exemplarily illustrated in Schemes 1-3 shown below. Therein R has one of the meanings of $R^1$ given in formula I, and is for example H, or alkyl or fluorinated alkyl with 1 to 20 C-atoms that is straight-chain or branched.

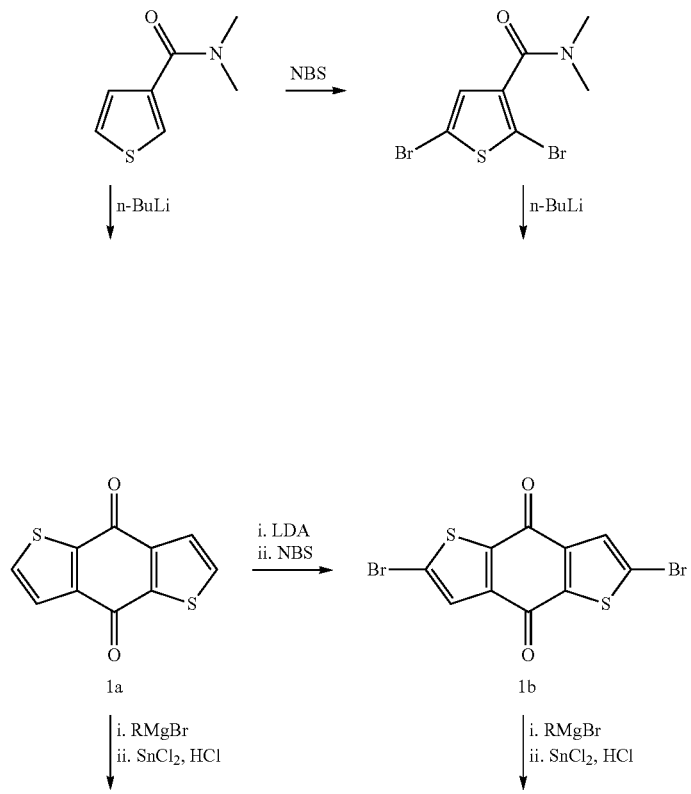

-continued

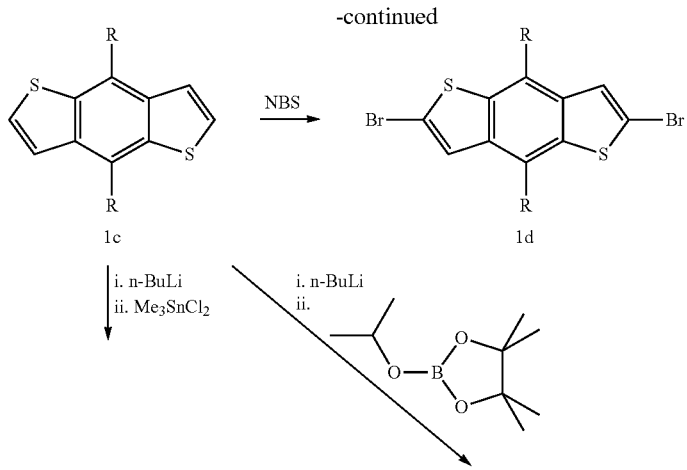

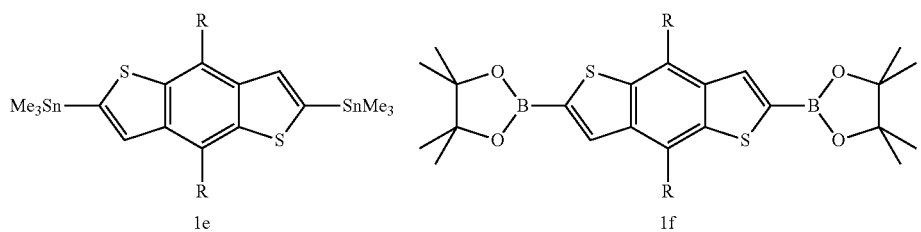

The synthesis of 2,6-dibromo-4,8-dialkylbenzo[1,2-b:4,5-b'] dithiophene (1b) is outlined in Scheme 1 starting from N,N-dimethyl-thiophene-3-carboxamide. Alternatively, N,N-diethyl-thiophene-3-carboxamide can also be used. N,N-Dimethyl-thiophene-3-carboxamide is treated with 1 equivalent of n-butyllithium to yield 4,8-dihydrobenzo[1,2-b:4,5-b']dithiophene-4,8-dione (1a) (Slocum and Gierer, *J. Org. Chem.* 1976, 41, 3668). This product is treated with an alkyl Grignard reagent followed by stannous chloride and dilute hydrochloric acid to yield 4,8-dialkylbenzo[1,2-b:4,5-b']dithiophene (1c). Bromination of this product using NBS yields 2,6-dibromo-4,8-dialkylbenzo[1,2-b:4,5-b']dithiophene (1d).

An alternative pathway also outlined in Scheme 1 involves treatment of N,N-dimethyl-thiophene-3-carboxamide with NBS to yield N,N-dimethyl-2,5-dibromothiophene-3-carboxamide, which is is treated with 1 equivalent of n-butyllithium to yield 2,6-dibromo-4,8-dihydrobenzo[1,2-b:4,5-b']dithiophene-4,8-dione (1b) (Slocum and Gierer, *J. Org. Chem.* 1976, 41, 3668). This product is treated with an alkyl Grignard reagent followed by stannous chloride and dilute hydrochloric acid to yield 2,6-dibromo-4,8-dialkylbenzo[1,2-b:4,5-b']dithiophene (1d).

Alternatively, the 4,8-dialkylbenzo[1,2-b:4,5-b']dithiophene product (1c) can be treated with n-butyllithium followed by trimethyltin chloride to yield the bis-trimethylstannane product (1e) or n-butyllithium followed by 2-isopropoxy-4,4,5,5-tetramethyl-1,3,2-dioxaborolane to yield the bis-pinacolatoboronate product (1f)

Furthermore, 4,8-dihydrobenzo[1,2-b:4,5-b']dithiophene-4,8-dione (1a) can be converted to 2,6-dibromo-4,8-dihydrobenzo[1,2-b:4,5-b']dithiophene-4,8-dione (1b) as shown in Scheme 1. This is done by a double lithiation with a hindered amine base such as LDA (lithium diisopropylamide) followed by reaction with an electrophillic source of bromine such as NBS.

The benzo[1,2-b:4,5-b']dithiophene-4,8-dicarboxylic acid alkyl ester (1c), wherein R=carbonyloxyalkyl (e.g. —$COOC_{12}H_{25}$), can be prepared in analogy to the method described in Citterio et al., Tetrahedron 1996, 13227-13242. The corresponding 2,6-dibromo product (1d), 2,6-bis-trimethylstannate (1e) or 2,6-bis-pinacolatoboronate (1f), wherein R=carbonyloxyalkyl (e.g. —$COOC_{12}H_{25}$), can then be synthesized from (1c) by the methods described in Scheme 1.

Scheme 2

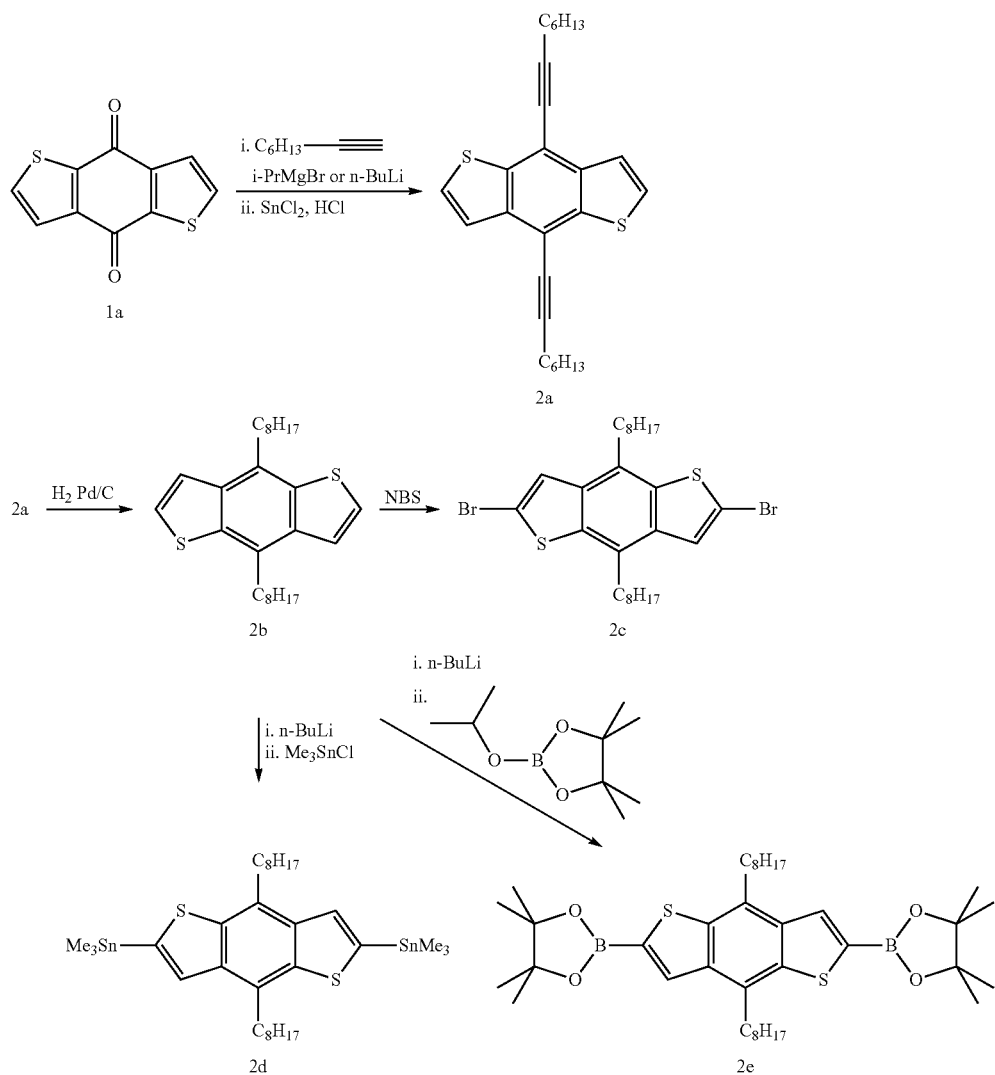

Another alternative route is as reported by by H. Pan, Y. Li, Y. Wu, P. Liu, B. S. Ong, S. Zhu and G. Xu, *Chem. Mat.*, 2006, 18, 3237 where 4,8-dihydrobenzo[1,2-b:4,5-b']dithiophene-4,8-dione (1a) is treated as outlined in Scheme 1 with the acetylene Grignard reagent (formed from the acetylene and isoproylmagnesium bromide) followed by stannous chloride and dilute hydrochloric acid. Alternatively, 4,8-dihydrobenzo[1,2-b:4,5-b']dithiophene-4,8-dione (1a) can be treated with the lithium acetylide (formed from the acetylene and n-butyllithium) followed by stannous chloride and dilute hydrochloric acid. The diacetylene product (2a) is hydrogenated over palladium on charcoal to form the dialkylated product (2b), which is brominated using NBS or using n-butyllithium followed by carbon tetrabromide to yield the dibromide product (2c).

As described above, the 4,8-dialkylbenzo[1,2-b:4,5-b']dithiophene product (2b) can alternatively be converted to the bis-trimethylstannane product (2d) or the bis-pinacolatoboronate product (2e) using the same methods as described for Scheme 1.

Scheme 3

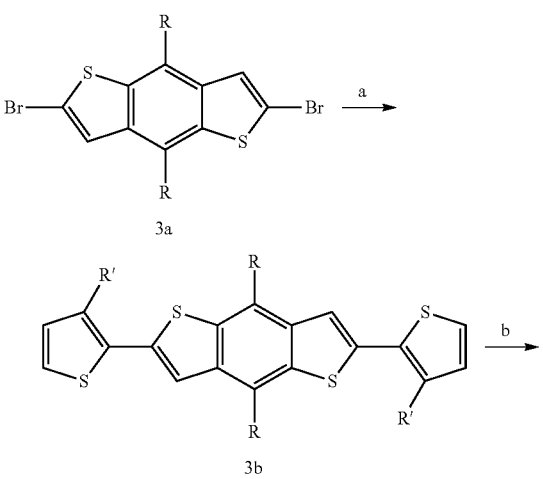

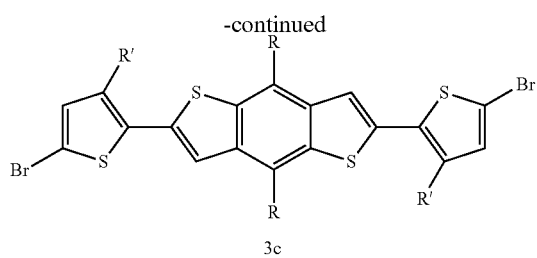

a) 2-Tributylstannyl(3-alkylthiophene), PdCl₂(PPh₃)₂;
b) i. n-BuLi or t-BuLi, ii. CBr₄

The synthesis of 2,6-bis(5-bromo-3-alkyl-2-thienyl)-4,8-dialkylbenzo[1,2-b:4,5-b']dithiophenes (3c) is outlined in Scheme 3. 2,6-Dibromo-4,8-dialkylbenzo[1,2-b:4,5-b']dithiophene (3a) is reacted with 2-tributyl-stannyl(3-alkylthiophene) in a palladium-catalysed Stille coupling to form the 2,6-bis(3-alkyl-2-thienyl)4,8-dialkylbenzo[1,2-b:4,5-b']dithiophene product (3b), which can be brominated by treatment with either n-butyllithium or t-butyllithium, followed by reaction with an electrophillic source of bromine such as carbon tetrabromide to yield the 2,6-bis(5-bromo-3-alkyl-2-thienyl)-4,8-dialkylbenzo[1,2-b:4,5-b']dithiophene product (3c).

The polymers can be synthesized by various organometallic catalyzed reaction such as Yamamoto coupling (see e.g. Yamamoto, T.; Morita, A.; Miyazaki, Y.; Maruyama, T.; Wakayama, H.; Zhou, Z. H.; Nakamura, Y.; Kanbara, T.; Sasaki, S.; Kubota, K. *Macromolecules* 1992, 25, 1214-1223, and Yamamoto, T.; Takimiya, K. *J. Am. Chem. Soc.* 2007, 129, 2224-2225), Suzuki coupling (see e.g. Schlüter, A. D. *J. Polym. Sci., Part A: Polym. Chem.* 2001, 39, 1533-1556), or Stille coupling (see e.g. Bao, Z.; Chan, W. K.; Yu, L. *J. Am. Chem. Soc.* 1995, 117, 12426-12435). The homopolymers are preferably synthesized using Yamamoto or Suzuki coupling, as illustrated in the Schemes below.

Suitable methods for the homopolymerisation and copolymerisation are exemplarily illustrated in Schemes 4-7 below, where $R^{1-4}$, Ar, n and R' as defined in formula I and Ia, Ar' has one of the meanings of Ar, and a=0 and b=1 or a=1 and b=0. Therein a thiophene ring can also be replaced by a selenophene, dithiophene or diselenophene group or by a group of formula IIb or IIc as defined above.

Scheme 4-Synthesis of homopolymers:

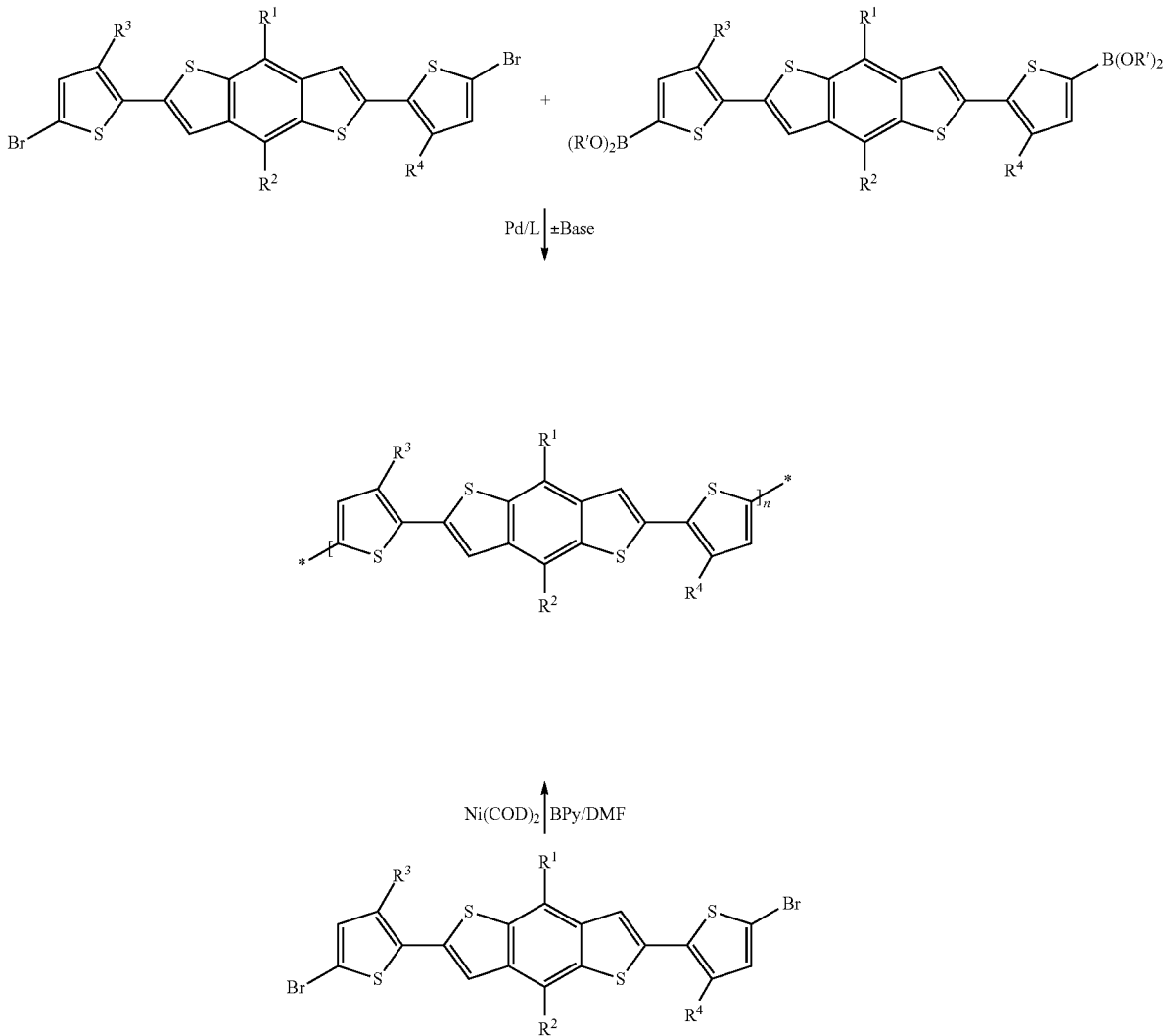

Scheme 5-Synthesis of alternating co-polymers:
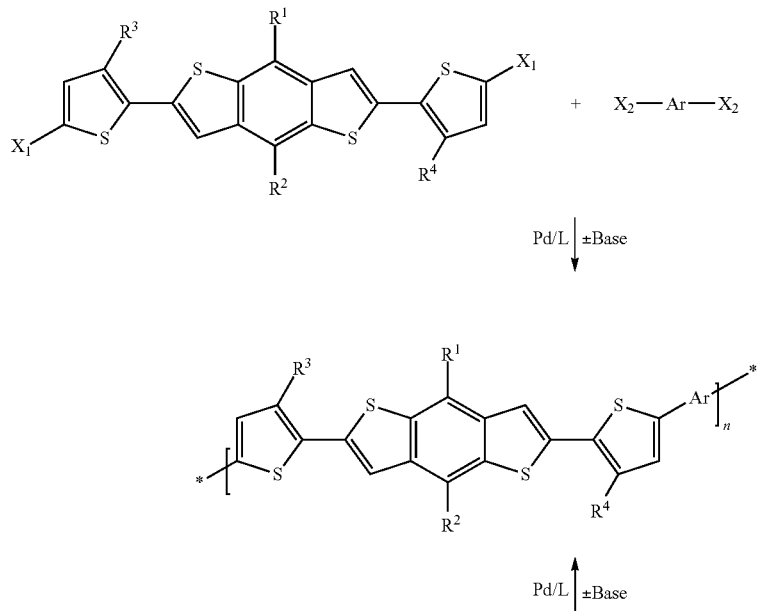
$X_1 = Br; X_2 = B(OR')_2$
$X_1 = B(OR')_2; X_2 = Br$
$X_1 = Br; X_2 = SnR'_3$
$X_1 = SnR'_3; X_2 = Br$
40
Scheme 6-Synthesis of random co-polymers:
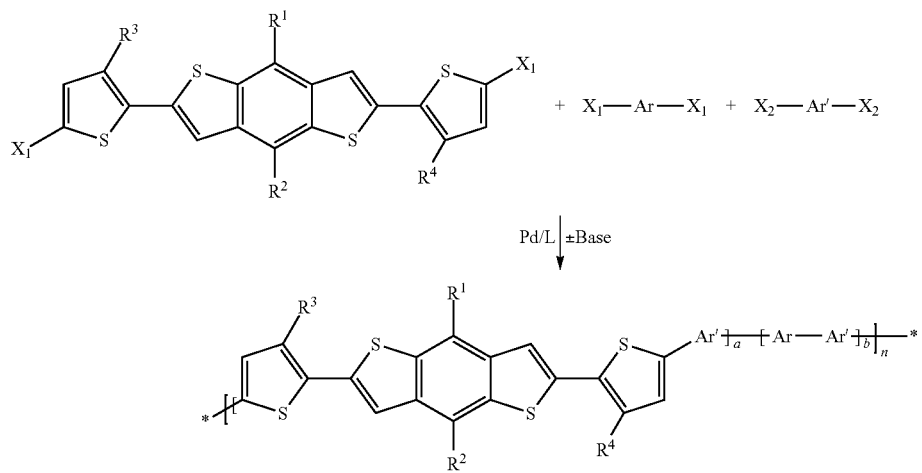
$X_1 = Br; X_2 = B(OR')_2$
$X_1 = Br; X_2 = SnR'_3$
$X_1 = B(OR')_2; X_2 = Br$ Scheme 7-Synthesis of random co-polymers:

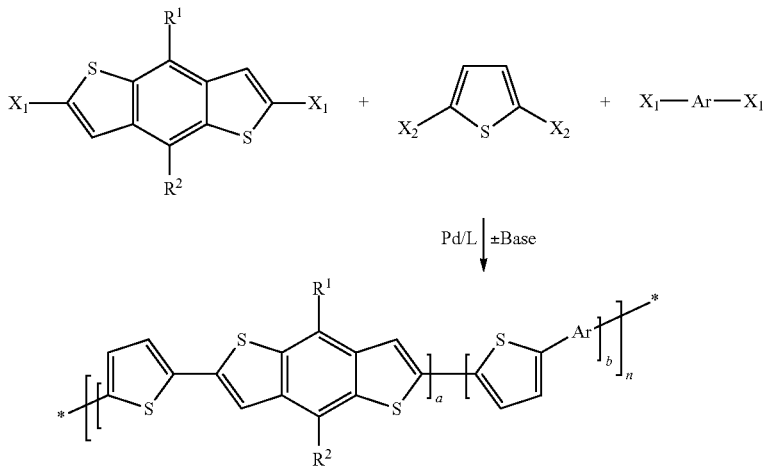

$X_1 = Br; X_2 = B(OR')_2$
$X_1 = B(OR')_2; X_2 = Br$
$X_1 = Br; X_2 = SnR'_3$
$X_1 = SnR'_3; X_2 = Br$

The novel methods of preparing monomers and polymers as described above and below are another aspect of the invention.

The polymers according to the present invention can also be used in polymer blends, for example together with other polymers having charge-transport, semiconducting, electrically conducting, photoconducting and/or light emitting semiconducting properties, or for example with polymers having hole blocking or electron blocking properties for use as interlayers or charge blocking layers in OLED devices. Thus, another aspect of the invention relates to a polymer blend comprising one or more polymers according to the present invention and one or more further polymers having one or more of the above-mentioned properties. These blends can be prepared by conventional methods that are described in prior art and known to the skilled person. Typically the polymers are mixed with each other or dissolved in suitable solvents and the solutions combined.

Another aspect of the invention relates to a formulation comprising one or more polymers or polymer blends as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetramethyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, dimethylformamide, 2-chloro-6fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylansiole, 3-methylanisole, 4-fluoro-3-methylanisole, 2-fluorobenzonitrile, 4-fluoroveratrol, 2,6-dimethylanisole, 3-fluorobenzonitrile, 2,5-dimethylanisole, 2,4-dimethylanisole, benzonitrile, 3,5-dimethylanisole, N,N-dimethylaniline, ethyl benzoate, 1-fluoro-3,5-dimethoxybenzene, 1-methylnaphthalene, N-methylpyrrolidinone, 3-fluorobenzotrifluoride, benzotrifluoride, benzotrifluoride, diosane, trifluoromethoxybenzene, 4-fluorobenzotrifluoride, 3-fluoropyridine, toluene, 2-fluorotoluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluorobenzene, 3-chlorofluorobenzene, 1-chloro-2,5-difluorobenzene, 4-chlorofluorobenzene, chlorobenzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents with high boiling temperatures and solvent mixtures are preferred. For spin coating alkylated benzenes like xylene and toluene are preferred.

Examples of especially preferred solvents include, without limitation, dichloromethane, trichloromethane, monochlorobenzene, o-dichlorobenzene, tetrahydrofuran, anisole, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, dimethylformamide, dimethylacetamide, dimethylsulfoxide, tetraline, decaline, indane, methyl benzoate, ethyl benzoate, mesitylene and/or mixtures thereof.

The concentration of the polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., Journal of Paint Technology, 38, No 496, 296 (1966)". Solvent blends may also be used and can be identified as described in "Solvents, W. H. Ellis, Federation of Societies for Coatings Technology, p9-10, 1986". Such a procedure may lead to a blend of 'non' solvents that will dissolve both the polymers of the present invention, although it is desirable to have at least one true solvent in a blend.

The polymers according to the present invention can also be used in patterned OSC layers in the devices as described above and below. For applications in modern microelectronics it is generally desirable to generate small structures or patterns to reduce cost (more devices/unit area), and power consumption. Patterning of thin layers comprising a polymer according to the present invention can be carried out for example by photolithography, electron beam lithography or laser patterning.

For use as thin layers in electronic or electrooptical devices the polymers, polymer blends or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, letter-press printing, screen printing, doctor blade coating, roller printing, reverse-roller printing, offset lithography printing, flexographic printing, web printing, spray coating, brush coating or pad printing. Ink-jet printing is particularly preferred as it allows high resolution layers and devices to be prepared.

Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents method above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer according to the present invention by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the polymer, which reduces or prevents clogging of the jets and separation of the components during spraying. The solvent(s) may include those selected from the following list of examples: dodecylbenzene, 1-methyl-4-tert-butylbenzene, terpineol limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The polymers or formulations according to the present invention can additionally comprise one or more further components or additives selected for for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The polymers according to the present invention are useful as charge transport, semiconducting, electrically conducting, photoconducting or light mitting materials in optical, electrooptical, electronic, electroluminescent or photoluminescent components or devices. In these devices, the polymers of the present invention are typically applied as thin layers or films.

Thus, the present invention also provides the use of the semiconducting polymer, polymer blend, formulation or layer in an electronic device. The formulation may be used as a high mobility semiconducting material in various devices and apparatus. The formulation may be used, for example, in the form of a semiconducting layer or film. Accordingly, in another aspect, the present invention provides a semiconducting layer for use in an electronic device, the layer comprising a polymer, polymer blend or formulation according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising a polymer, polymer blend, formulation or organic semiconducting layer according to the present invention. Especially preferred devices are OFETs, TFTs, ICs, logic circuits, capacitors, RFID tags, OLEDs, OLETs, OPEDs, OPVs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs and OPV devices, in particular bulk heterojunction (BHJ) OPV devices. In an OFET, for example, the active semiconductor channel between the drain and source may comprise the layer of the invention. As another example, in an OLED device, the charge (hole or electron) injection or transport layer may comprise the layer of the invention.

For use in OPV devices the polymer according to the present invention is preferably used in a formulation that comprises or contains, more preferably consists essentially of, very preferably exclusively of, a p-type (electron donor) semiconductor and an n-type (electron acceptor) semiconductor. The p-type semiconductor is constituted by a polymer according to the present invention. The n-type semiconductor can be an inorganic material such as zinc oxide or cadmium selenide, or an organic material such as a fullerene derivate, for example (6,6)-phenyl-butyric acid methyl ester derivatized methano $C_{60}$ fullerene, also known as "PCBM" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or an structural analogous compound with e.g. a $C_{70}$ fullerene group ($C_{70}$PCBM), or a polymer (see for example Coakley, K. M. and McGehee, M. D. *Chem. Mater.* 2004, 16, 4533).

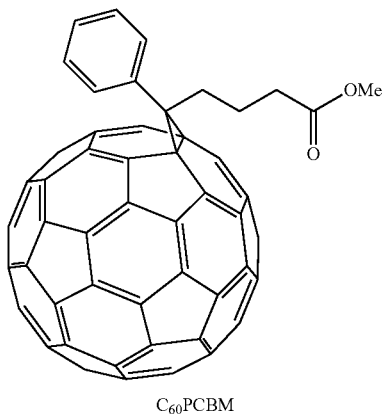 [SMILES: COC(=O)CCCC1(c2ccccc2)C23C=C4Cc5cc6cc7c8c9c(cc%10cc%11c%12c(c%13c%14c%15c(c4c5c4c6c8c(c%154)c4c9c%10c%12c%144)C%1321)C(=C3)C%11)C7]

$C_{60}$PCBM

A preferred material of this type is a blend or mixture of a polymer according to the present invention with a $C_{60}$ or $C_{70}$ fullerene or modified fullerene like PCBM. Preferably the ratio polymer:fullerene is from 2:1 to 1:2 by weight, more preferably from 1.2:1 to 1:1.2 by weight, most preferably 1:1 by weight. For the blended mixture, an optional annealing step may be necessary to optimize blend morphology and consequently OPV device performance.

The OPV device can for example be of any type known from the literature [see e.g. Waldauf et al., Appl. Phys. Lett. 89, 233517 (2006)].

A typical and preferred OPV device according to the present invention, comprises:
  a low work function electrode (for example a metal, such as aluminum), and a high work function electrode (for example ITO), one of which is transparent,
  a layer (also referred to as "active layer") comprising a hole transporting material and an electron transporting material, preferably selected from OSC materials, situated between the electrodes; the active layer can exist for example as a bilayer or two distinct layers or blend or mixture of p-type and n-type semiconductor, forming a bulk heterjunction (BHJ) (see for example Coakley, K. M. and McGehee, M. D. *Chem. Mater.* 2004, 16, 4533),
  an optional conducting polymer layer, for example comprising a blend of PEDOT:PSS (poly(3,4-ethylenedioxythiophene): poly(styrenesulfonate)), situated between the active layer and the high work function electrode, to modify the work function of the high work function electrode to provide an ohmic contact for holes,
  an optional coating (for example of LiF) on the side of the low workfunction electrode facing the active layer (13), to provide an ohmic contact for electrons.

A typical and preferred inverted OPV device according to the present invention, comprising:
  a low work function electrode (for example a metal, such as gold), and a high work function electrode (for example ITO), one of which is transparent,
  a layer (also referred to as "active layer") comprising a hole transporting material and an electron transporting material, preferably selected from OSC materials, situated between the electrodes; the active layer can exist for example as a bilayer or two distinct layers or blend or mixture of p-type and n-type semiconductor, forming a BHJ,
  an optional conducting polymer layer, for example comprising a blend of PEDOT:PSS, situated between the active layer and the low work function electrode to provide an ohmic contact for electrons,
  an optional coating (for example of $TiO_x$) on the side of the high workfunction electrode facing the active layer, to provide an ohmic contact for holes.

In the OPV devices of the present invent invention, the p-type and n-type semiconductor materials are preferably selected from the materials, like the polymer/fullerene systems, as described above. If the bilayer is a blend an optional annealing step may be necessary to optimize device performance.

The compound, formulation and layer of the present invention are also suitable for use in an OFET as the semiconducting channel. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a polymer, polymer blend, formulation or organic semiconducting layer according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these FETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:
  a source electrode,
  a drain electrode,
  a gate electrode,
  a semiconducting layer,
  one or more gate insulator layers,
  optionally a substrate.
  wherein the semiconductor layer preferably comprises a polymer, polymer blend or formulation as described above and below.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass).

Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetry value, like stamps, tickets, shares, cheques etc.

Alternatively, the materials according to the invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and films may be employed in one or more of the charge transport layers and/or in the emission layer, corresponding to their electrical and/or optical properties. Furthermore their use within the emission layer is especially advantageous, if the compounds, materials and films according to the invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Meerholz, Synthetic Materials, 111-112, 2000, 31-34, Alcala, J. Appl. Phys., 88, 2000, 7124-7128 and the literature cited therein.

According to another use, the materials according to the present invention, especially those which show photoluminescent properties, may be employed as materials of light sources, e.g., of display devices such as described in EP 0 889 350 A1 or by C. Weder et al., Science, 279, 1998, 835-837.

A further aspect of the invention relates to both the oxidised and reduced form of the compounds according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $ASF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)$ $(SbF_6^-)$, $(NO_2^+)$ $(SbCl_6^-)$, $(NO_2^+)$ $(BF_4^-)$, $AgClO_4$, $H_2IrCl_6$, $La(NO_3)_3.6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds of the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The compounds and formulations according to the present invention amy also be suitable for use in organic plasmon-emitting diodes (OPEDs), as described for example in Koller et al., Nature Photonics 2008 (published online Sep. 28, 2008).

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material. The compounds or materials according to the present invention having mesogenic or liquid crystalline properties can form oriented anisotropic films as described above, which are especially useful as alignment layers to induce or enhance alignment in a liquid crystal medium provided onto said anisotropic film. The materials according to the present invention may also be combined with photoisomerisable compounds and/or chromophores for use in or as photoalignment layers, as described in US 2003/0021913.

According to another use the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W.

McBranch, H. Wang, R. Helgeson, F. Wudl and D. G. Whitten, Proc. Natl. Acad. Sci. U.S.A. 1999, 96, 12287; D. Wang, X. Gong, P. S. Heeger, F. Rininsland, G. C. Bazan and A. J. Heeger, Proc. Natl. Acad. Sci. U.S.A. 2002, 99, 49; N. DiCesare, M. R. Pinot, K. S. Schanze and J. R. Lakowicz, Langmuir 2002, 18, 7785; D. T. McQuade, A. E. Pullen, T. M. Swager, Chem. Rev. 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention. Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

It will be appreciated that many of the features described above, particularly of the preferred embodiments, are inventive in their own right and not just as part of an embodiment of the present invention. Independent protection may be sought for these features in addition to or alternative to any invention presently claimed.

The invention will now be described in more detail by reference to the following examples, which are illustrative only and do not limit the scope of the invention.

EXAMPLE 1

Poly{5,5-[2,6-bis[(3-hexyl)-2-thienyl]-4,8-didodecylbenzo[1,2-b:4,5-b']dithiophene]-alt-4,7-(2,1,3-benzothiadiazole)}(1) was Prepared as Follows

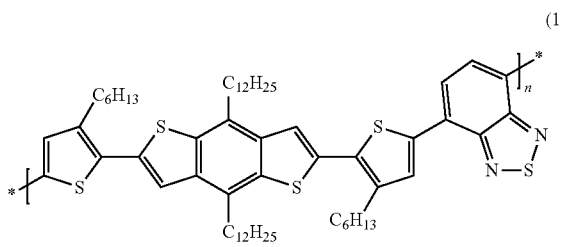

(1)

1.1 2,6-Dibromo-4,8-didodecylbenzo[1,2-b:4,5-b']dithiophene

A 1.0M solution of dodecylmagnesium bromide in diethyl ether (17.5 mL, 17.5 mmol) was added dropwise to a stirred suspension of 2,6-dibromo-4,8-dihydrobenzo[1,2-b:4,5-b']dithiophene-4,8-dione (2.00 g, 5.29 mmol) in anhydrous THF (70 mL) under $N_2$. The mixture was stirred at 23° C. for 18 h. Stannous(II) chloride (5.02 g, 26.45 mmol) and 37% hydrochloric acid (10 mL) were added and the mixture was stirred for 6 hours. Water (150 mL) was added and the resulting precipitate was filtered off and dried under vacuum. The crude product was purified by column chromatography on silica gel (eluent: petroleum ether 40-60) and recrystallisation twice from acetone to yield the product as a white solid (0.77 g, 21%): $^1$H NMR (300 MHz, $CDCl_3$, ppm) 7.41 (s, 2H, Ar—H), 2.99 (t, J=8 Hz, 4H, $CH_2$), 1.73 (m, 4H, $CH_2$), 1.19-1.47 (m, 36H, $CH_2$), 0.88 (t, J =7 Hz, 6H, $CH_3$).

1.2 2,6-Bis[(3-hexyl)-2-thienyl]-4,8-didodecylbenzo[1,2-b:4,5-b']dithiophene

To a degassed mixture of 2,6-dibromo-4,8-didodecylbenzo[1,2-b:4,5-b']dithiophene (5.14 g, 7.50 mmol), 2-tributylstannyl(3-hexylthiophene) (8.23 g, 18.00 mmol) and anhydrous DMF (150 cm$^3$) was added dichlorobis(triphenylphosphine)palladium(II) (0.26 g, 0.38 mmol) and the mixture was further degassed with $N_2$ for 5 minutes. The mixture was heated to 100° C. and stirred for 17 hours. After cooling to 23° C., water (100 cm$^3$) was added and the product was extracted into DCM (2×500 cm$^3$). The combined extracts were dried over anhydrous magnesium sulfate, filtered and concentrated in vacuo. The crude product was filtered through silica gel (eluent: petroleum ether 40:60:DCM; 70:30) and recrystallised from THF/methanol to yield the product as an orange solid (3.79 g, 59%): $^1$H NMR (300 MHz, $CDCl_3$, ppm) 7.42 (s, 2H, Ar—H), 7.26 (d, J=5 Hz, 2H, Ar—H), 6.99 (d, J=5 Hz, 2H, Ar—H), 3.14 (t, J=8 Hz, 4H, $CH_2$), 2.88 (t, J=8 Hz, 4H, $CH_2$), 1.83 (m, 4H, $CH_2$), 1.70 (m, 4H, $CH_2$), 1.18-1.52 (m, 48H, $CH_2$), 0.87 (m, 12H, $CH_3$).

1.3 2,6-Bis[(5-bromo-3-hexyl)-2-thienyl]-4,8-didodecylbenzo[1,2-b:4,5-b']dithiophene To a solution of 2,6-bis[(3-hexyl)2-thienyl]-4,8-didodecylbenzo[1,2-b:4,5-b']dithiophene (1.05 g, 1.22 mmol) in anhydrous THF (50 cm$^3$) at 0° C. was added dropwise a 1.6M solution of n-butyllithium in hexanes (1.5 cm$^3$, 2.40 mmol) under $N_2$. The mixture was stirred at 0° C. for 20 minutes before cooling to −78° C. and the addition of a solution of carbon tetrabromide (0.85 g, 2.57 mmol) in anhydrous THF (20 cm$^3$) over a period of 1 minute. The mixture was allowed to warm to 23° C. over a period of 1 hour. The mixture was poured into water (200 cm$^3$) and the product was extracted into DCM (2×250 cm$^3$). The combined extracts were dried over anhydrous magnesium sulfate, filtered and concentrated in vacuo. The crude product was purified by column chromatography on silica gel (eluent: petroleum ether 40-60) and recrystallisation from petrol 80-100 to yield the product as a bright yellow solid (0.59 g, 47%): $^1$H NMR (300 MHz, $CDCl_3$, ppm) 7.36 (s, 2H, Ar—H), 6.95 (s, 2H, Ar—H), 3.11 (t, J=8 Hz, 4H, $CH_2$), 2.82 (t, J=8 Hz, 4H, $CH_2$), 1.80 (m, 4H, $CH_2$), 1.66 (m, 4H, $CH_2$), 1.19-1.51 (m, 48H, $CH_2$), 0.87 (m, 12H, $CH_3$).

1.4 Poly{5,5-[2,6-bis[(3-hexyl)-2-thienyl]-4,8-didodecylbenzo[1,2-b:4,5-b']dithiophene]-alt-4,7-(2,1,3-benzothiadiazole)}(1)

To a mixture of 2,6-bis[(5-bromo-3-hexyl)-2-thienyl]-4,8-didodecylbenzo-[1,2-b:4,5-b']dithiophene (0.500 g, 0.492 mmol), 4,7-bis(4,4,5,5-tetramethyl-1,3,2-dioxaborolan-2- yl)-2,1,3-benzothiadiazole (0.191 g, 0.492 mmol), tris (dibenzylideneacetone)dipalladium(0) (9 mg, 0.010 mmol) and tri(o-tolyl)phosphine (12 mg, 0.039 mmol) in toluene (10 cm$^3$) was added Aliquat 336 (50 mg). The mixture was degassed with N$_2$ at 23° C. A degassed 2M aqueous solution of sodium carbonate (0.75 cm$^3$, 1.50 mmol) was added. The mixture was heated to reflux and stirred for 1 hour. After cooling to 23° C., the mixture was precipitated from stirred methanol (100 cm$^3$) and the polymer was collected by filtration and washed with methanol (20 cm$^3$). The polymer was washed via Soxhlet extraction with acetone, cyclohexane, DCM, and chlorobenzene. The chlorobenzene extract was reduced in volume in vacuo and precipitated from stirred methanol (50 cm$^3$). The polymer was collected by filtration, washed with methanol (20 cm$^3$), water (20 cm$^3$) and methanol (20 cm$^3$), and vacuum dried to yield the product as a black solid (70 mg, 14%).

EXAMPLE 2

Poly{5,5-[2,6-bis[(3-hexyl)-2-thienyl]-4,8-di(2-ethylhexyl)benzo[1,2-b:4,5-b']dithiophene]-alt-4,7-(2,1,3-benzothiadiazole)} (2) was Prepared as Follows

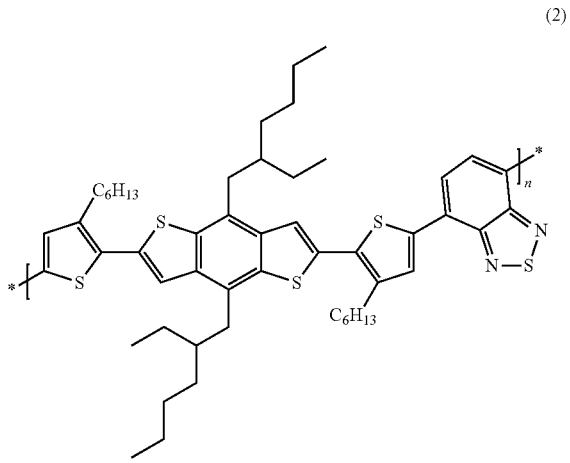

(2)

2.1 2,6-Dibromo-4,8-di(2-ethylhexyl)benzo[1,2-b:4,5-b']dithiophene

2-Ethylhexylmagnesium bromide was prepared from 2-ethylhexylbromide (21.50 g, 111.33 mmol) and magnesium (2.80 g, 116.67 mmol) in anhydrous THF (100 mL) with initiation by crystals of iodine. The solution of 2-ethylhexylmagnesium bromide was added dropwise to a stirred suspension of 2,6-dibromo-4,8-dihydrobenzo[1,2-b:4,5-b']dithiophene-4,8-dione (21.00 g, 55.55 mmol) in anhydrous THF (210 mL) under N$_2$. The mixture was stirred at 23° C. for 16 hours and at 67° C. for 6 hours. After cooling to 23° C., stannous(II) chloride (52.60 g, 277.28 mmol) was added and the mixture was stirred for 30 minutes. 37% hydrochloric acid (100 mL) was added and the mixture was stirred for 16 h. The mixture was poured into water (800 mL) and extracted into ethyl acetate (500 mL). The organic extract was washed with 5% hydrochloric acid (2×1 L), dried over sodium sulphate, and concentrated in vacuo. The crude product was purified by column chromatography on silica gel (eluent: petroleum ether 40-60) and trituration with acetonitrile to yield the product as a white solid (2.20 g, 7%): $^1$H NMR (300 MHz, CDCl$_3$, ppm) 7.41 (s, 2H, Ar—H), 2.88 (m, 4H, CH$_2$), 1.85 (m, 2H, CH$_2$), 1.17-1.45 (m, 16H, CH$_2$), 0.87 (m, 12H, CH$_3$).

2.2 2,6-Bis[(3-hexyl)-2-thienyl]-4,8-di(2-ethylhexyl)benzo[1,2-b:4,5-b']dithiophene To a degassed mixture of 2,6-dibromo-4,8-(2-ethylhexyl)benzo[1,2-b:4,5-b']dithiophene (3.07 g, 5.36 mmol), 2-tributylstannyl(3-hexylthiophene) (5.89 g, 12.87 mmol) and anhydrous DMF (100 cm$^3$) was added dichlorobis(triphenyl-phosphine)palladium(II) (0.19 g, 0.27 mmol) and the mixture was further degassed with N$_2$ for 5 minutes. The mixture was heated to 100° C. for 65 hours. After cooling to 23° C., water (500 cm$^3$) was added and the product was extracted into DCM (2×350 cm$^3$). The combined extracts were dried over anhydrous magnesium sulfate, filtered and concentrated in vacuo. The crude product was filtered through silica gel (eluent: petroleum ether 40:60:DCM; 80:20) to yield the product as a bright yellow oil (3.36 g, 84%): $^1$H NMR (300 MHz, CDCl$_3$, ppm) 7.42 (s, 2H, Ar—H), 7.25 (d, J=5 Hz, 2H, Ar—H), 6.99 (d, J=5 Hz, 2H, Ar—H), 3.08 (m, 4H, CH$_2$), 2.88 (t, J=8 Hz, 4H, CH$_2$), 1.99 (m, 2H, CH), 1.24-1.77 (m, 32H, CH$_2$), 0.84-0.96 (m, 18H, CH$_3$).

2.3 2,6-Bis[(5-bromo-3-hexyl)-2-thienyl]-4,8-di(2-ethylhexyl)benzo[1,2-b:4,5-b']dithiophene To a solution of 2,6-bis[(3-hexyl)2-thienyl]-4,8-di(2-ethylhexyl)benzo[1,2-b:4,5-b']dithiophene (0.65 g, 0.79 mmol) in anhydrous THF (30 cm$^3$) at −78° C. was added dropwise a 1.7M solution of t-butyllithium in pentane (1.4 cm$^3$, 2.38 mmol) under N$_2$. The mixture was stirred for 15 minutes before the addition of carbon tetrabromide (0.57 g, 1.73 mmol). The mixture was stirred at −78° C. for 20 minutes and methanol (40 cm$^3$) was added followed by stirring for 10 minutes. The product collected by filtration and washed with methanol (20 cm$^3$), water (50 cm$^3$) and methanol (20 cm$^3$). The crude product was purified by column chromatography on silica gel (eluent: petroleum ether 40-60) to give a yellow oil, which solidified upon standing (0.44 g, 62%): $^1$H NMR (300 MHz, CDCl$_3$, ppm) 7.36 (s, 2H, Ar—H), 6.94 (s, 2H, Ar—H), 3.05 (m, 4H, CH$_2$), 2.81 (t, J=8 Hz, 4H, CH$_2$), 1.95 (m, 2H, CH), 1.66 (m, 4H, CH$_2$), 1.24-1.47 (m, 28H, CH$_2$), 0.83-0.96 (m, 18H, CH$_3$).

2.4 Poly{5,5-[2,6-bis[(3-hexyl)-2-thienyl]-4,8-di(2-ethylhexyl)benzo[1,2-b:4,5-b']dithiophene]-alt-4,7-(2,1,3-benzothiadiazole)} (2)

To a mixture of 2,6-bis[(5-bromo-3-hexyl)-2-thienyl]-4,8-di(2-ethylhexyl)benzo-[1,2-b:4,5-b']dithiophene (0.350 g, 0.387 mmol), 4,7-bis(4,4,5,5-tetramethyl-1,3,2-dioxaborolan-2-yl)-2,1,3-benzothiadiazole (0.150 g, 0.387 mmol), tris (dibenzylideneacetone)dipalladium(0) (7 mg, 0.008 mmol) and tri(o-tolyl)phosphine (9 mg, 0.031 mmol) in toluene (8 cm$^3$) was added Aliquat 336 (50 mg). The mixture was degassed with N$_2$ at 23° C. A degassed 2M aqueous solution of sodium carbonate (0.60 cm$^3$, 1.20 mmol) was added. The mixture was heated to reflux and stirred for 4 hours. After cooling to 23° C., the mixture was precipitated from stirred methanol (100 cm$^3$) and the polymer was collected by filtration and washed with methanol (20 cm$^3$), water (20 cm$^3$) and methanol (20 cm$^3$). The polymer was washed via Soxhlet extraction with acetone, cyclohexane, and chlorobenzene. The chlorobenzene extract was reduced in vacuo to a smaller volume and precipitated from methanol (50 cm$^3$). The polymer was collected by filtration, washed with methanol (20 cm$^3$), and vacuum dried to yield the product as a black solid (30 mg, 9%). GPC (Chlorobenzene ("PhCl"), 60° C.) $M_w$=12,500 g/mol, $M_n$=7,700 g/mol.

EXAMPLE 3

Poly{5,5-[2,6-bis[3-(2-hexyldecyl)-2-thienyl]-4,8-di(2-ethylhexyl)benzo[1,2-b:4,5-b']dithiophene]-alt-4,7-(2,1,3-benzothiadiazole)} (3) was Prepared as Follows

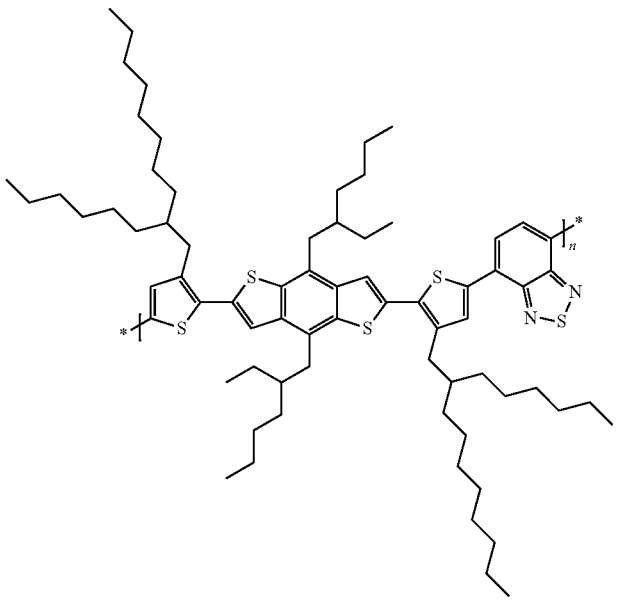

(3)

3.1 3-(2-Hexyldecyl)thiophene

A solution of 7-bromomethyl-pentadecane (34.00 g, 111.4 mmol) in anhydrous tetrahydrofuran (180 cm$^3$) was added dropwise to a mixture of magnesium turnings (2.70 g, 111.0 mmol), a crystal of iodine and anhydrous tetrahydrofuran (20 cm$^3$). The reaction mixture was heated at 67° C. for 4 hours. The formed Grignard solution was allowed to cool to 23° C. and a mixture of 3-bromothiophene (5.49 g, 33.6 mmol) and [1,1'-bis(diphenylphosphino)ferrocene]dichloropalladium(II) (1.10 g, 1.35 mmol) was added dropwise over 5 minutes. The reaction mixture was heated at 67° C. for 17 hours. The mixture was allowed to cool and poured into water (400 cm$^3$) and the product was extracted with dichloromethane (2×300 cm$^3$). The combined organic extracts were dried over anhydrous magnesium sulfate, filtered and the solvent was removed in vacuo. The crude product was purified by column chromatography (40-60 petrol) to give the product as a colourless oil (10.94 g, 89%): MS (m/e): 308 (M$^+$, 10%), 223, 195, 98.

3.2 2-Bromo-3-(2-hexyldecyl)thiophene

To a mixture of 3-(2-hexyldecyl)thiophene (9.90 g, 32.1 mmol) in anhydrous tetrahydrofuran (200 cm$^3$) was added N-bromosuccinimide (5.78 g, 32.1 mmol) in one portion. The reaction mixture was heated at 67° C. for 17 hours. The solvent was removed in vacuo and the residue was purified by column chromatography (eluent: 40-60 petroleum ether) to give the product as a colourless oil (12.04 g, 95%): MS (m/e): 386, 388 (M$^+$, 20%), 307.

3.3 Tributyl[3-(2-hexyldecyl)-2-thienyl]stannane

To a flask containing magnesium turnings (0.55 g, 22.71 mmol), one crystal of iodine and anhydrous tetrahydrofuran (5 cm$^3$) was added 2.5 cm$^3$ of a solution of 2-bromo-3-(2-hexyldecyl)thiophene (8.00 g, 20.65 mmol) in anhydrous tetrahydrofuran (50 cm$^3$) and the reaction was gently warmed until initiation. The remaining tetrahydrofuran solution was added dropwise. After addition, the reaction mixture was heated at 67° C. for 2 hours. The formed Gignard solution was cooled to 23° C. and added dropwise to a solution of tributyl tin chloride (6.7 cm$^3$, 24.70 mmol) in anhydrous tetrahydrofuran (30 cm$^3$) at 23° C. The reaction mixture was stirred at 23° C. for 17 hours before addition to ice (100 cm$^3$) and extraction into diethyl ether (2×200 cm$^3$). The combined extracts were dried over anhydrous magnesium sulfate, filtered and the solvent was removed in vacuo to give the product as a yellow oil (12.34 g, 100%), which was used without further purification: $^1$H NMR (300 MHz, CDCl$_3$, ppm) 7.53 (d, J=5 Hz, 1H, Ar—H), 7.05 (s, J=5 Hz, 1H, Ar—H), 2.50-2.55 (m, 2H, CH$_2$), 0.84-1.70 (m, 58H, CH$_3$, CH$_2$, CH).

3.4 2,6-Bis[3-(2-hexyldecyl)-2-thienyl]-4,8-di(2-ethylhexyl)benzo[1,2-b;4,5-b']dithiophene To a degassed mixture of 2,6-dibromo-4,8-di(2-ethylhexyl)benzo[1,2-b;4,5-b']dithiophene (4.93 g, 8.60 mmol), tributyl-[3-(2-hexyldecyl)-2-thienyl]stannane (12.34 g, 20.65 mmol) and anhydrous N,N-dimethylformamide (200 cm$^3$) was added bis(triphenylphosphine)-palladium(II) chloride (0.30 g, 0.43 mmol) and the reaction mixture was further degassed for 5 minutes. The reaction mixture was heated at 100° C. for 17 hours before cooling to 23° C. Water (1000 cm³) was added and the product was extracted into dichloromethane (3×500 cm³). The combined extracts were washed with water (1000 cm³), dried over anhydrous magnesium sulfate, filtered and the solvent was removed in vacuo. The crude product was purified by column chromatography (eluent: 40-60 petroleum ether) to give the product as a yellow oil (6.68 g, 76%): $^1$H NMR (300 MHz, CDCl₃, ppm) 7.42 (s, 2H, Ar—H), 7.25 (d, J=5 Hz, 2H, Ar—H), 6.95 (d, J=5 Hz, 2H, Ar—H), 2.99-3.15 (m, 4H, CH₂), 2.79-2.88 (m, 4H, CH₂), 1.92-2.05 (m, 2H, CH), 1.69-1.80 (m, 2H, CH), 1.09-1.51 (m, 64H, CH₂), 0.79-0.98 (m, 24H, CH₂).

3.5 2,6-Bis[5-bromo-3-(2-hexyldecyl)-2-thienyl]-4,8-di(2-ethylhexyl)benzo[1,2-b;4,5-b']dithiophene To a mixture of 2,6-bis[3-(2-hexyldecyl)-2-thienyl]-4,8-di(2-ethylhexyl)benzo[1,2-b;4,5-b']dithiophene (4.40 g, 4.28 mmol) and anhydrous tetrahydrofuran (200 cm³) at −78° C. was added dropwise t-butyllithium (5.0 cm³, 8.5 mmol, 1.7M in pentane). The reaction mixture was stirred at −78° C. for 15 minutes and carbontetrabromide (3.12 g, 9.42 mmol) was added. The reaction mixture stirred at −78° C. for 20 minutes and methanol (40 cm³) was added followed by stirring at 23° C. for 30 minutes. Water (500 cm³) was added and the product was extracted into dichloromethane (2×500 cm³). The combined extracts were dried over anhydrous magnesium sulfate, filtered and the solvent was removed in vacuo. The crude product was purified by column chromatography (eluent: 40-60 petroleum ether) to give the product as a yellow oil (2.96 g, 58%): $^1$H NMR (300 MHz, CDCl₃, ppm) 7.37 (s, 2H, Ar—H), 6.90 (s, 2H, Ar—H), 2.96-3.12 (m, 4H, CH₂), 2.71-2.81 (m, 4H, CH₂), 1.89-2.02 (m, 2H, CH), 1.63-1.74 (m, 2H, CH), 1.11-1.49 (m, 64H, CH₂), 0.79-0.97 (m, 24H, CH₂).

3.6 Poly{5,5-[2,6-bis[3-(2-hexyldecyl)-2-thienyl]-4,8-di(2-ethylhexyl)benzo[1,2-b;4,5-b']dithiophene]-alt-4,7-(2,1,3-benzothiadiazole)}

To a mixture of 2,6-bis-[5-bromo-3-(2-hexyldecyl)-2-thienyl]-4,8-di(2-ethylhexyl)benzo[1,2-b;4,5-b']dithiophene (0.800 g, 0.675 mmol), 4,7-bis(4,4,5,5-tetramethyl-1,3,2-dioxaborolan-2-yl)-2,1,3-benzothiadiazole (0.262 g, 0.657 mmol), tris(dibenzylideneacetone)dipalladium (0) (12 mg, 0.013 mmol) and tri(o-tolyl) phosphine (16 mg, 0.054 mmol) in toluene (15 cm³) was added Aliquat 336 (50 mg). The reaction mixture was degassed for 30 minutes. A degassed 2M aqueous solution of sodium carbonate (1.0 cm³, 2.0 mmol) and the reaction mixture was further degassed for 5 minutes. The reaction mixture was heated at 110° C. for 41 hours. The solution was allowed to cool to 23° C. and precipitated into stirred methanol (100 cm³). The polymer was collected by filtration and washed with methanol (20 cm³). The crude polymer was washed via Soxhlet extraction with acetone, methanol, 40-60 petroleum ether and cyclohexane. The cyclohexane fraction was poured into methanol (200 cm³) and the polymer precipitate was collected by filtration, washed with methanol (20 cm³) to the product as a black solid (0.550 g, 70%): GPC (PhCl, 60° C.) $M_w$=39,300 g/mol, $M_n$=14,400 g/mol.

EXAMPLE 4

Poly{5,5-[2,6-bis(2-thienyl)-4,8-dioctylbenzo[1,2-b:4,5-b']dithiophene]-alt-4,7-(5,6-dioctyloxy)-2,1,3-benzothiadiazole} (4) was Prepared as Follows

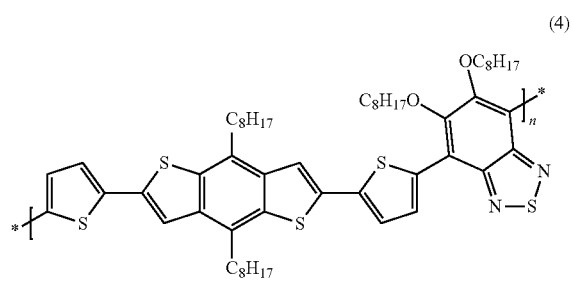

(4)

4,8-Dioctyl-benzo[1,2-b;4,5-b']dithiophene was prepared in an analogous manner to the report by H. Pan, Y. Li, Y. Wu, P. Liu, B. S. Ong, S. Zhu and G. Xu, *Chem. Mat.*, 2006, 18, 3237.

4,7-bis(5-bromo-2-thienyl)-5,6-bis(octyloxy)-2,1,3-benzothiadiazole was prepared following the report by R. Qin, W. Li, C. Li, C. Du, C. Veit, H.-F. Schleiermacher, M. Andersson, Z. Bo, Z. Liu, O. Inganas, U. Wuerfel and F. Zhang, *J. Am. Chem. Soc.*, 2009, 131, 14612.

4.1 2,6-Bis(trimethylstannyl)-4,8-dioctylbenzo-[1,2-b:4,5-b']dithiophene 4,8-Dioctyl-benzo[1,2-b;4,5-b']dithiophene (1.50 g, 3.62 mmol) was dissolved in anhydrous THF (60 cm³) and the solution was cooled to −78° C. under N₂. n-Butyllithium solution (3.0 cm³, 7.5 mmol, 2.5M in hexanes) was added dropwise over 10 minutes and the resulting mixture was stirred at −78° C. for 30 minutes and then at 23° C. for 30 minutes. The reaction mixture was cooled to −78° C. and trimethyltinchloride solution (8.0 cm³, 8.0 mmol, 1.0M in THF) was added in one portion. The cooling bath was removed and the resulting mixture was stirred at 23° C. for 2 hours before pouring into water and extacting into diethyl ether three times. The combined extracts were dried over sodium sulfate and concentrated in vacuo. The crude product was recrystallised from iso-propanol to yield the product as white crystals (1.81 g, 68%): $^1$H NMR (300 MHz, CDCl₃, ppm) 7.50 (s, 2H, Ar—H), 3.21 (t, J=8 Hz, 4H, CH₂), 1.82 (m, 4H, CH₂), 1.21-1.54 (m, 20H, CH₂), 0.89 (t, J=7 Hz, 6H, CH₃), 0.46 (s, 18H, CH₃).

4.2 Poly{5,5-[2,6-bis(2-thienyl)-4,8-dioctyl)benzo[1,2-b:4,5-b']dithiophene]-alt-4,7-(5,6-dioctyloxy)-2,1,3-benzothiadiazole} (4)

A mixture of 2,6-bis(trimethylstannyl)-4,8-dioctylbenzo-[1,2-b:4,5-b']dithiophene (0.740 g, 1.000 mmol), 4,7-bis(5-bromo-2-thienyl)-5,6-bis(octyloxy)-2,1,3-benzothiadiazole (0.715 g, 1.000 mmol), tris(dibenzyl-ideneacetone)dipalladium(0) (9 mg, 0.010 mmol) and tri(o-tolyl)phosphine (12 mg, 0.040 mmol) was subjected to three evacuation-filling cycles with N₂. Degassed anhydrous toluene (12 cm³) and anhydrous DMF (3 cm³) were added. The reaction mixture was heated in a microwave reactor (Intitiator, Biotage AB) at 120° C. (2 minutes), 140° C. (2 minutes), 160° C. (2 minutes) and 180° C. (20 minutes). The reaction mixture was precipitated from methanol and the crude polymer was collected by filtration and washed with methanol. The polymer was washed via Soxhlet extraction with acetone and then 40-60 petroleum ether before extraction into chloroform and then chlorobenzene. The chloroform extract was reduced to a smaller volume, precipitated from methanol, and the polymer was collected by filtration, washed with methanol, and dried under vacuum to yield the product as a black solid (0.213 g, 22%). The chlorobenzene extract was reduced to a smaller volume, precipitated from methanol, and the polymer was collected by filtration, washed with methanol, and dried under vacuum to yield the product as a black solid (0.183 g, 19%). GPC (1,2,4-trichlorobenzene, 140° C.): $M_w$=44,200 g/mol; $M_n$=25,500 g/mol.

EXAMPLE 5

Poly{[2,6-(2-thienyl)-4,8-di(2-ethylhexyl)benzo[1,2-b:4,5-b']dithiophene]-co-4,7-(2-thienyl)-5,6-dioctyloxy-2,1,3-benzothiadiazole} (5) was Prepared as Follows

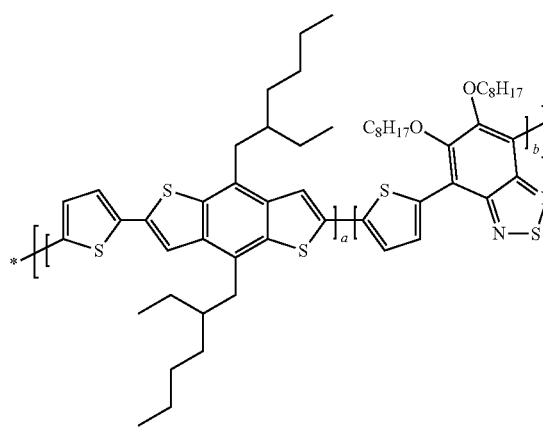

(5)

5.1 Poly{[2,6-(2-thienyl)-4,8-di(2-ethylhexyl)benzo[1,2-b:4,5-b']dithiophene]-co-4,7-(2-thienyl)-5,6-dioctyloxy-2,1,3-benzothiadiazole} (5)

A solution of 2,6-dibromo-4,8-(2-ethylhexyl)benzo[1,2-b:4,5-b']dithiophene (0.172 g, 0.300 mmol), 2,5-(trimethylstannyl)thiophene (0.246 g, 0.600 mmol), 4,7-dibromo-5,6-dioctyloxy-2,1,3-benzothiadiazole (0.165 g, 0.300 mmol), tris(dibenzylideneacetone)dipalladium(0) (11 mg, 0.012 mmol), tri(o-tolyl)phosphine (15 mg, 0.048 mmol) and chlorobenzene (10 cm³) was prepared and degassed with N₂ for 5 minutes. The reaction mixture was heated in a microwave reactor (Intitiator, Biotage AB) at 140° C. (1 minute), 160° C. (1 minute), 170° C. (0.5 minutes), and 180° C. (30 minutes). The reaction mixture was precipitated into a mixture of 37% hydrochloric acid (10 cm³) and methanol (100 cm³), and stirred for 10 minutes. The crude polymer collected by filtration and washed with methanol (100 cm³). The polymer was washed via Soxhlet extraction with acetone, methanol, 40-60 petroleum ether, and then cyclohexane before extraction into chloroform. The chloroform extract was reduced to a smaller volume, precipitated from methanol, and the polymer was collected by filtration, washed with methanol, and dried under vacuum to yield the product as a black solid (0.170 g, 59%): GPC (PhCl, 60° C.) $M_w$=42,200 g/mol, $M_n$=26,700 g/mol.

EXAMPLE 6

Poly{[2,6-(2-selenophenyl)-4,8-di(2-ethylhexyl)benzo[1,2-b:4,5-b']dithiophene]-co-4,7-(2-selenophenyl)-5,6-dioctyloxy-2,1,3-benzothiadiazole} (6) was Prepared as Follows

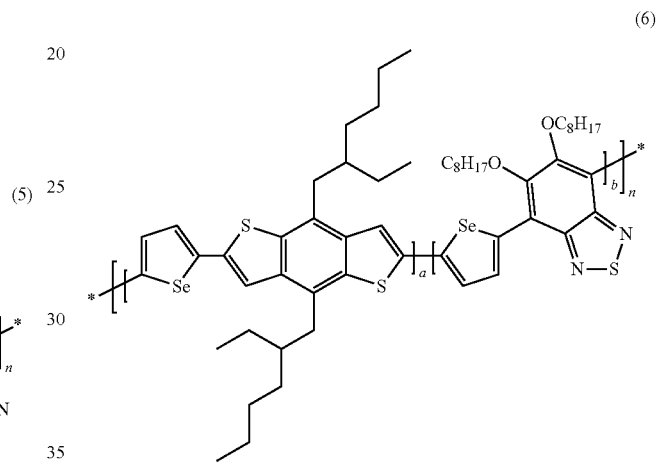

(6)

6.1 Poly{[2,6-(2-selenophenyl)-4,8-di(2-ethylhexyl)benzo[1,2-b:4,5-b']dithiophene]-co-4,7-(2-selenophenyl)-5,6-dioctyloxy-2,1,3-benzothiadiazole} (6)

A solution of 2,6-dibromo-4,8-(2-ethylhexyl)benzo[1,2-b:4,5-b']dithiophene (0.344 g, 0.600 mmol), 2,5-bis(trimethylstannyl)selenophene (0.548 g, 1.200 mmol), 4,7-dibromo-5,6-dioctyloxy-2,1,3-benzothiadiazole (0.330 g, 0.600 mmol), tris(dibenzylideneacetone)dipalladium(0) (22 mg, 0.024 mmol), tri(o-tolyl)phosphine (29 mg, 0.096 mmol) and chlorobenzene (15 cm³) was prepared and degassed with N₂ for 5 minutes. The reaction mixture was heated in a microwave reactor (Intitiator, Biotage AB) at 140° C. (1 minute), 160° C. (1 minute), and 170° C. (30 minutes). The reaction mixture was precipitated into a mixture of 37% hydrochloric acid (10 cm³) and methanol (100 cm³), and stirred for 10 minutes. The crude polymer collected by filtration and washed with methanol. The polymer was washed via Soxhlet extraction with acetone, methanol, 40-60 petroleum ether, and then cyclohexane before extraction into chloroform. The chloroform extract was precipitated from methanol and the polymer was collected by filtration, washed with methanol, and dried under vacuum to yield the product as a black solid (0.340 g, 53%): GPC (PhCl, 60° C.) $M_w$=21,800 g/mol, $M_n$=12,900 g/mol.

EXAMPLE 7

Poly{[2,6-(5-bithophenyl)-4,8-di(2-ethylhexyl)benzo[1,2-b:4,5-b']dithiophene]-co-4,7-(5-bithiophenyl)-5,6-dioctyloxy-2,1,3-benzothiadiazole} (7) was Prepared as Follows

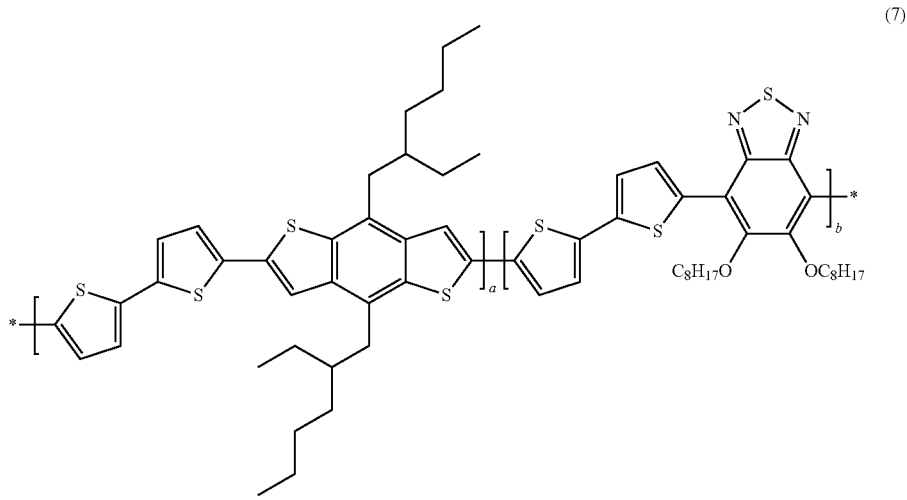

(7)

7.1 Poly{[2,6-(5-bithophenyl)-4,8-di(2-ethylhexyl)benzo[1,2-b:4,5-b']dithiophene]-co-4,7-(5-bithiophenyl)-5,6-dioctyloxy-2,1,3-benzothiadiazole} (7)

A solution of 2,6-dibromo-4,8-(2-ethylhexyl)benzo[1,2-b:4,5-b']dithiophene (0.344 g, 0.600 mmol), 5,5-bis(trimethylstannyl)bithiophene (0.590 g, 1.200 mmol), 4,7-dibromo-5,6-dioctyloxy-2,1,3-benzothiadiazole (0.330 g, 0.600 mmol), tris(dibenzylideneacetone)dipalladium(0) (22 mg, 0.024 mmol), tri(o-tolyl)phosphine (29 mg, 0.096 mmol) and chlorobenzene (15 cm³) was prepared and degassed with $N_2$ for 5 minutes. The reaction mixture was heated in a microwave reactor (Intitiator, Biotage AB) at 140° C. (1 minute), 160° C. (1 minute), and 170° C. (30 minutes). The reaction mixture was precipitated into a mixture of 37% hydrochloric acid (10 cm³) and methanol (100 cm³), and stirred for 10 minutes. The crude polymer collected by filtration and washed with methanol. The polymer was washed via Soxhlet extraction with acetone, methanol, 40-60 petroleum ether, cyclohexane, and then chloroform before extraction into chlorobenzene. The chlorobenzene extract was precipitated from methanol and the polymer was collected by filtration, washed with methanol, and dried under vacuum to yield the product as a black solid (0.420 g, 62%).

EXAMPLE 8

Poly{[2,6-(2-thieno[3,2-b]phenyl)-4,8-di(2-ethylhexyl)benzo[1,2-b:4,5-b']dithiophene]-co-4,7-(2-thieno[3,2-b]thiophenyl)-5,6-dioctyloxy-2,1,3-benzothiadiazole} (8) was Prepared as Follows

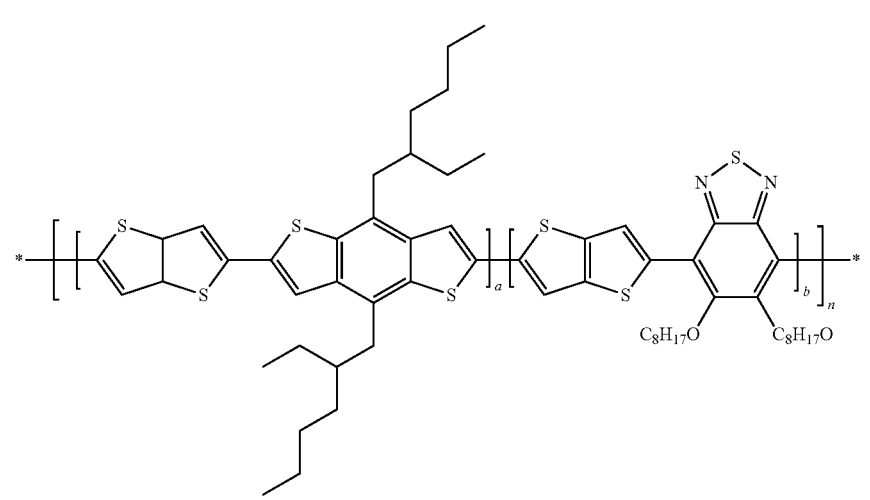

(8)

8.1 Poly{[2,6-(2-thieno[3,2-b]phenyl)-4,8-di(2-eth-ylhexyl)benzo[1,2-b:4,5-b']dithiophene]-co-4,7-(2-thieno[3,2-b]phenyl)-5,6-dioctyloxy-2,1,3-benzothiadiazole} (8)

A solution of 2,6-dibromo-4,8-(2-ethylhexyl)benzo[1,2-b:4,5-b']dithiophene (0.172 g, 0.300 mmol), 2,5-bis(trimethylstannyl)thieno[3,2-b]thiophene (0.280 g, 0.600 mmol), 4,7-dibromo-5,6-dioctyloxy-2,1,3-benzothiadiazole (0.165 g, 0.300 mmol), tris(dibenzylideneacetone)dipalladium(0) (11 mg, 0.012 mmol), tri(o-tolyl)phosphine (15 mg, 0.048 mmol) and chlorobenzene (15 cm³) was prepared and degassed with $N_2$ for 5 minutes. The reaction mixture was heated in a microwave reactor (Intitiator, Biotage AB) at 140° C. (1 minute), 160° C. (1 minute), and 170° C. (30 minutes). The reaction mixture was precipitated into a mixture of 37% hydrochloric acid (10 cm³) and methanol (100 cm³), and stirred for 10 minutes. The crude polymer collected by filtration and washed with methanol. The polymer was washed via Soxhlet extraction with acetone, methanol, 40-60 petroleum ether, and then cyclohexane before extraction into chloroform. The chloroform extract was precipitated from methanol and the polymer was collected by filtration, washed with methanol, and dried under vacuum to yield the product as a black solid (0.150 g, 46%).

EXAMPLE 9

Poly{5,5-[2,6-bis(2-thienyl)-4,8-di(dodecyl)benzo[1,2-b:4,5-b']dithiophene]-alt-4,7-(5,6-dioctyloxy)-2,1,3-benzothiadiazole} (9) was Prepared as Follows

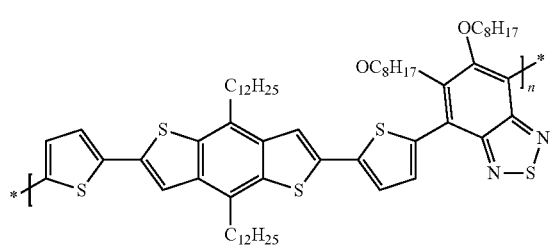

(9)

4,8-Di(dodecyl)benzo[1,2-b;4,5-b']dithiophene was prepared in an analogous manner to the report by H. Pan, Y. Li, Y. Wu, P. Liu, B. S. Ong, S. Zhu and G. Xu, *Chem. Mat.*, 2006, 18, 3237.

9.1 2,6-Bis(trimethylstannyl)-4,8-di(dodecyl)benzo-[1,2-b:4,5-b']dithiophene 4,8-Di(dodecyl)benzo[1,2-b;4,5-b']dithiophene (4.04 g, 7.67 mmol) was dissolved in anhydrous THF (120 cm³) and the solution was cooled to −78° C. under $N_2$. n-Butyllithium solution (9.2 cm³, 23.00 mmol, 2.5M in hexanes) was added dropwise over 10 minutes and the resulting mixture was stirred at −78° C. for 30 minutes and then at 23° C. for 30 minutes. The reaction mixture was cooled to −78° C. and trimethyltinchloride solution (24.5 cm³, 24.50 mmol, 1.0M in THF) was added in one portion. The cooling bath was removed and the resulting mixture was stirred at 23° C. for 2 hours before pouring into water and extacting into diethyl ether three times. The combined extracts were dried over sodium sulfate and concentrated in vacuo. The crude product was recrystallised from iso-propanol to yield the product as white crystals (4.29 g, 66%): ¹H NMR (300 MHz, CDCl₃, ppm) 7.49 (s, 2H, Ar—H), 3.20 (t, J=8 Hz, 4H, CH₂), 1.83 (m, 4H, CH₂), 1.21-1.51 (m, 36H, CH₂), 0.88 (t, J=7 Hz, 6H, CH₃), 0.45 (s, 18H, CH₃).

9.2 Poly{5,5-[2,6-bis(2-thienyl)-4,8-di(dodecyl)benzo[1,2-b:4,5-b']dithiophene]-alt-4,7-(5,6-dioctyloxy)-2,1,3-benzothiadiazole} (9)

A mixture of 2,6-bis(trimethylstannyl)-4,8-di(dodecyl)benzo-[1,2-b:4,5-b']dithiophene (0.853 g, 1.000 mmol), 4,7-bis(5-bromo-2-thienyl)-5,6-bis(octyloxy)-2,1,3-benzothiadiazole (0.715 g, 1.000 mmol), tris(dibenzyl-ideneacetone)dipalladium(0) (5 mg, 0.005 mmol) and tri(o-tolyl)phosphine (6 mg, 0.020 mmol) was subjected to three evacuation-filling cycles with $N_2$. Degassed anhydrous toluene (12 cm³) and anhydrous DMF (3 cm³) were added. The reaction mixture was heated in a oil bath at 110° C. for 20 minutes. The reaction mixture was precipitated from methanol and the crude polymer was collected by filtration and washed with methanol. The polymer was washed via Soxhlet extraction with acetone and then 40-60 petroleum ether before extraction into chloroform and then chlorobenzene. The chloroform extract was reduced to a smaller volume, precipitated from methanol, and the polymer was collected by filtration, washed with methanol, and dried under vacuum to yield the product as a black solid (0.110 g, 10%). The chlorobenzene extract was reduced to a smaller volume, precipitated from methanol, and the polymer was collected by filtration, washed with methanol, and dried under vacuum to yield the product as a black solid (0.115 g, 11%). GPC (1,2,4-trichlorobenzene, 140° C.): $M_w$=42,000 g/mol; $M_n$=21,600 g/mol.

EXAMPLE 10

Poly{[2,6-(2-thienyl)-4,8-di(dodecyl)benzo[1,2-b:4,5-b']dithiophene]-co-4,7-(2-thienyl)-5,6-dioctyloxy-2,1,3-benzothiadiazole} (10) was Prepared as Follows

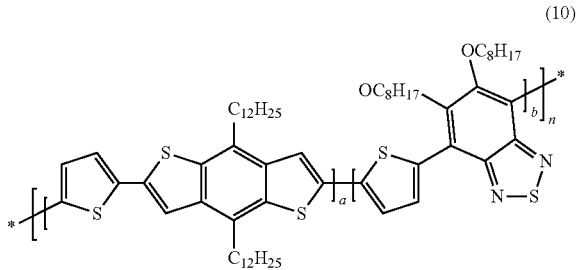

(10)

10.1 Poly{[2,6-(2-thienyl)-4,8-di(dodecyl)benzo[1,2-b:4,5-b']dithiophene]-co-4,7-(2-thienyl)-5,6-dioctyloxy-2,1,3-benzothiadiazole} (10)

A solution of 2,6-dibromo-4,8-(dodecyl)benzo[1,2-b:4,5-b']dithiophene (0.411 g, 0.600 mmol), 2,5-(trimethylstannyl)thiophene (0.492 g, 1.200 mmol), 4,7-dibromo-5,6-dioctyloxy-2,1,3-benzothiadiazole (0.330 g, 0.600 mmol), tris(dibenzylideneacetone)dipalladium(0) (22 mg, 0.024 mmol), tri(o-tolyl)phosphine (29 mg, 0.096 mmol) and chlorobenzene (15 cm³) was prepared and degassed with $N_2$ for 5 minutes. The reaction mixture was heated in a microwave reactor (Intitiator, Biotage AB) at 140° C. (1 minute), 160° C. (1 minute), 170° C. (0.5 minutes), and 180° C. (30 minutes). The reaction mixture was precipitated into a mixture of 37% hydrochloric acid (10 cm³) and methanol (100 cm³), and stirred for 10 minutes. The crude polymer collected by filtration and washed with methanol (100 cm³). The polymer was washed via Soxhlet extraction with acetone, methanol, 40-60 petroleum ether, and then cyclohexane before extraction into chloroform. The chloroform extract was reduced to a smaller volume, precipitated from methanol, and the polymer was collected by filtration, washed with methanol, and dried under vacuum to yield the product as a black solid (0.540 g, 83%): GPC (1,24-trichlorobenzene, 140° C.) $M_w$=56,100 g/mol, $M_n$=33,500 g/mol.

EXAMPLE 11

Poly{[2,6-(2-thienyl)benzo[1,2-b:4,5-b']dithiophene-4,8-dicarboxylic acid didodecyl ester]-co-4,7-(2-thienyl)-5,6-dioctyloxy-2,1,3-benzothiadiazole}(11) was Prepared as Follows

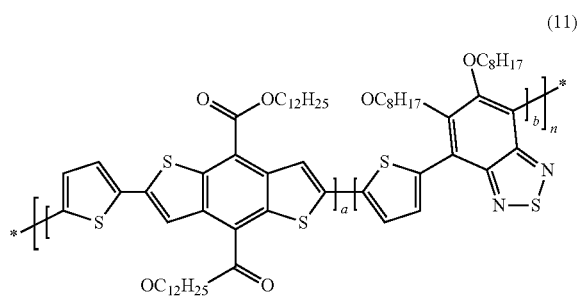

(11)

11.1 Poly{[2,6-(2-thienyl)benzo[1,2-b:4,5-b']dithiophene-4,8-dicarboxylic acid didodecyl ester]-co-4,7-(2-thienyl)-5,6-dioctyloxy-2,1,3-benzothiadiazole} (11)

A solution of 2,6-dibromobenzo[1,2-b:4,5-b']dithiophene-4,8-dicarboxylic acid didodecyl ester (0.464 g, 0.600 mmol), 2,5-bis(trimethylstannyl)thieno[3,2-b]thiophene (0.492 g, 1.200 mmol), 4,7-dibromo-5,6-dioctyloxy-2,1,3-benzothiadiazole (0.330 g, 0.600 mmol), tris(dibenzylideneacetone)dipalladium(0) (22 mg, 0.020 mmol), tri(o-tolyl)phosphine (29 mg, 0.096 mmol) in chlorobenzene (15 cm³) was prepared and degassed with $N_2$ for 5 minutes. The reaction mixture was heated in a microwave reactor (Intitiator, Biotage AB) at 140° C. (1 minute), 160° C. (1 minute), and 170° C. (30 minutes). The reaction mixture was precipitated into methanol (100 cm³) and stirred for 10 minutes. The crude polymer collected by filtration and washed with methanol (100 cm³). The polymer was washed via Soxhlet extraction with acetone, methanol, 40-60 petroleum ether, and then cyclohexane before extraction into chloroform. The chloroform extract was precipitated from methanol and the polymer was collected by filtration, washed with methanol, and dried under vacuum to yield the product as a black solid (0.500 g, 71%). GPC (1,2,4-trichlorobenzene, 140° C.): $M_w$=46,600 g/mol, $M_n$=22,300 g/mol.

EXAMPLE 12

Poly{[2,6-(2-thienyl)-4,8-di(dodecyl)benzo[1,2-b:4,5-b']dithiophene]-co-4,7-(2-thienyl)-5,6-dioctyloxy-2,1,3-benzooxadiazole} (12) was Prepared as Follows

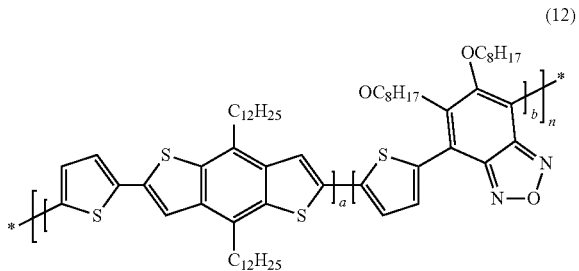

(12)

4,7-Dibromo-5,6-bis(octyloxy)-2,1,3-benzooxadiazole was prepared in an analogous manner to the report by J. Bouffard and T. M. Swager, *Macromolecules,* 2008, 41, 5559.

12.1 Poly{[2,6-(2-thienyl)-4,8-di(dodecyl)benzo[1,2-b:4,5-b']dithiophene]-co-4,7-(2-thienyl)-5,6-dioctyloxy-2,1,3-benzooxadiazole} (12)

A solution of 2,6-dibromo-4,8-(dodecyl)benzo[1,2-b:4,5-b']dithiophene (0.411 g, 0.600 mmol), 2,5-bis(trimethylstannyl)thieno[3,2-b]thiophene (0.492 g, 1.200 mmol), 4,7-dibromo-5,6-dioctyloxy-2,1,3-benzooxadiazole (0.321 g, 0.600 mmol), tris(dibenzylideneacetone)dipalladium(0) (22 mg, 0.020 mmol), tri(o-tolyl)phosphine (29 mg, 0.096 mmol) in chlorobenzene (15 cm³) was prepared and degassed with $N_2$ for 5 minutes. The reaction mixture was heated in a microwave reactor (Intitiator, Biotage AB) at 140° C. (1 minute), 160° C. (1 minute), and 170° C. (30 minutes). The reaction mixture was precipitated into a mixture of 37% hydrochloric acid (10 cm³) and methanol (100 cm³) and stirred for 10 minutes. The crude polymer collected by filtration and washed with methanol (100 cm³). The polymer was washed via Soxhlet extraction with acetone and 40-60 petroleum ether before extraction into cyclohexane. The cyclohexane extract was precipitated from methanol and the polymer was collected by filtration, washed with methanol, and dried under vacuum to yield the product as a black solid (0.599 g, 94%). GPC (1,2,4-trichlorobenzene, 140° C.): $M_w$=59,400 g/mol, $M_n$=27,200 g/mol.

EXAMPLE 13

Poly{[2,6-(2-thienyl)benzo[1,2-b:4,5-b']dithiophene-4,8-dicarboxylic acid didodecyl ester]-co-4,7-(2-thienyl)-5,6-didodecyloxy-2,1,3-benzothiadiazole} (13) was Prepared as Follows 2,6-dibromobenzo[1,2-b:4,5-b']dithiophene-4,8-dicarboxylic acid didodecyl ester was prepared in analogy to the method reported by Citterio et al., Tetrahedron 1996, 13227-13242, followed by bromination with NBS as described in Scheme 1 above.

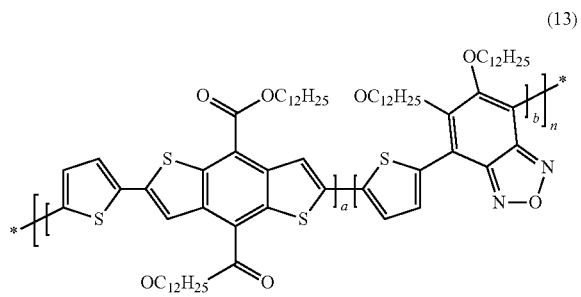

(13)

4,7-Dibromo-5,6-bis(dodecyloxy)-2,1,3-benzooxadiazole was prepared in an analogous manner to the report by J. Bouffard and T. M. Swager, *Macromolecules,* 2008, 41, 5559.

13.1 Poly{[2,6-(2-thienyl)benzo[1,2-b:4,5-b']dithiophene-4,8-dicarboxylic acid didodecyl ester]-co-4,7-(2-thienyl)-5,6-didodecyloxy-2,1,3-benzothiadiazole} (13)

A solution of 2,6-dibromobenzo[1,2-b:4,5-b']dithiophene-4,8-dicarboxylic acid didodecyl ester (0.464 g, 0.600 mmol), 2,5-bis(trimethylstannyl)thieno[3,2-b]thiophene (0.492 g, 1.200 mmol), 4,7-dibromo-5,6-didodecyloxy-2,1,3-benzooxadiazole (0.388 g, 0.600 mmol), tris(dibenzylideneacetone)dipalladium(0) (22 mg, 0.020 mmol), tri(o-tolyl)phosphine (29 mg, 0.096 mmol) in chlorobenzene (15 cm³) was prepared and degassed with $N_2$ for 5 minutes. The reaction mixture was heated in a microwave reactor (Initiator, Biotage AB) at 140° C. (1 minute), 160° C. (1 minute), and 170° C. (30 minutes). The reaction mixture was precipitated into a mixture of 37% hydrochloric acid (10 cm³) and methanol (100 cm³) and stirred for 10 minutes. The crude polymer collected by filtration and washed with methanol (100 cm³). The polymer was washed via Soxhlet extraction with acetone and 40-60 petroleum ether before extraction into chloroform. The chloroform extract was precipitated from methanol and the polymer was collected by filtration, washed with methanol, and dried under vacuum to yield the product as a blue solid (0.723 g, 52%). GPC (1,2,4-trichlorobenzene, 140° C.): $M_w$=63,100 g/mol, $M_n$=26,300 g/mol.

EXAMPLE 14

Transistor Fabrication and Measurement

Top-gate thin-film organic field-effect transistors (OFETs) were fabricated on glass substrates with photolithographically defined Au source-drain electrodes. A 1 wt. % solution of polymer in o-dichlorobenenzene was spin-coated ontop followed by a spin-coated fluoropolymer dielectric material (D139). Finally a photolithographically defined Au gate electrode was deposited. The electrical characterization of the transistor devices was carried out in ambient air atmosphere using computer controlled Agilent 4155C Semiconductor Parameter Analyser.

Charge carrier mobilities for polymer examples (4) and (10)-(13) in the saturation regime ($\mu_{sat}$) were calculated and are shown in table 1. Field-effect mobility was calculated in the saturation regime ($V_d$>($V_g$-$V_0$)) using equation (1):

$$\left(\frac{dI_d^{sat}}{dV_g}\right)_{V_d} = \frac{WC_i}{L}\mu^{sat}(V_g - V_0) \quad (1)$$

where W is the channel width, L the channel length, $C_i$ the capacitance of insulating layer, $V_g$ the gate voltage, $V_0$ the turn-on voltage, and $\mu_{sat}$ is the charge carrier mobility in the saturation regime. Turn-on voltage ($V_0$) was determined as the onset of source-drain current.

TABLE 1

| Transistor characteristics | |
|---|---|
| Polymer Example | Saturated mobility ($\mu_{sat}$) |
| (4) | 4 × 10⁻² cm²/Vs |
| (10) | 7 × 10⁻² cm²/Vs |
| (11) | 1 × 10⁻² cm²/Vs |
| (12) | 6 × 10⁻³ cm²/Vs |
| (13) | 1.2 × 10⁻² cm²/Vs |

EXAMPLE 15

Photovoltaic Cell Fabrication and Measurement

Organic photovoltaic (OPV) devices were fabricated on ITO-glass substrates (13 Ω/sq.) purchased from LUMTEC Corporation. Substrates were cleaned using common solvents (acetone, iso-propanol, deionized-water) in an ultrasonic bath prior to a conventional photolithography process that was carried out to define the bottom electrodes (anodes). A conducting polymer poly(ethylene dioxythiophene) doped with poly(styrene sulfonic acid) [Clevios VPAI 4083 (H. C. Starck)] was mixed in a 1:1 ratio with deionized-water. This solution was sonicated for 20 minutes to ensure proper mixing and filtered using a 0.2 μm filter before spin-coating to achieve a thickness of 20 nm. Substrates were exposed to ozone prior to the spin-coating process to ensure good wetting properties. Films were then annealed at 130° C. for 30 minutes in a nitrogen atmosphere where they were kept for the remainder of the process.

Active materials solutions were prepared at the concentration and components ratio stated in the examples and stirred overnight. Thin films were either spin-coated or blade-coated in a nitrogen atmosphere to achieve active layer thicknesses between 100 and 200 nm as measured using a profilometer. A short drying period followed to ensure removal of any residual solvent. Typically, spin-coated films were dried at 23° C. for 10 minutes and blade-coated films were dried at 70° C. for 3 minutes on a hotplate. For the last step of the device fabrication, Ca (30 nm)/Al (200 nm) cathodes were thermally evaporated through a shadow mask to define the cells.

Samples were measured at 23° C. under the irradiation of 1 Sun using a Solar Simulator (Newport Ltd, Model 91160) as the light source and using a calibrated Si-cell as the reference.

OPV device characteristics for blends of polymer examples (3)-(13) with $PC_{61}BM$ or $PC_{71}BM$ under irradiation of 1 Sun are shown in table 2.

TABLE 2

| Blend | η (%) | FF | $V_{oc}$ (mV) | $J_{sc}$ (mA/cm$^2$) |
|---|---|---|---|---|
| (3): PC$_{61}$BM | 0.2 | 40 | 480 | 1 |
| (4): PC$_{61}$BM | 3.7 | 60 | 670 | 9.25 |
| (4): PC$_{71}$BM | 4.25 | 60 | 675 | 10.50 |
| (5): PC$_{61}$BM | 3.85 | 48.75 | 820 | 9.63 |
| (6): PC$_{61}$BM | 3.54 | 43.50 | 755 | 10.75 |
| (7): PC$_{61}$BM | 3.1 | 64.75 | 720 | 6.5 |
| (8): PC$_{61}$BM | 1.82 | 40.56 | 730 | 6.15 |
| (9): PC$_{61}$BM | 3.45 | 64.5 | 770 | 7.01 |
| (9): PC$_{71}$BM | 4.2 | 70.25 | 800 | 7.38 |
| (10): PC$_{61}$BM | 5.4 | 70 | 800 | 9.65 |
| (10): PC$_{71}$BM | 6 | 70 | 785 | 10.95 |
| (11): PC$_{61}$BM | 6.1 | 76.3 | 810 | 10 |
| (11): PC$_{71}$BM | 6.3 | 73.25 | 800 | 10.8 |
| (12): PC$_{61}$BM | 1.8 | 53.4 | 770 | 4.35 |
| (13): PC$_{61}$BM | 1.4 | 60.3 | 830 | 2.80 |

The invention claimed is:

1. A polymer of formula I

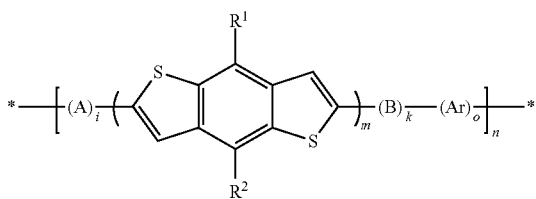

wherein

A is on each occurrence identically or differently one of the following groups

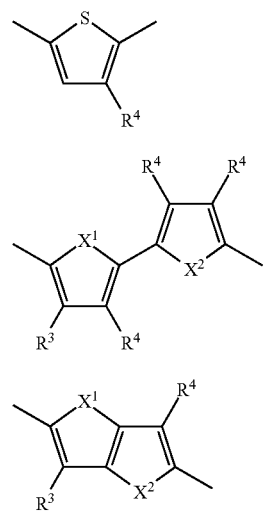

B is on each occurrence identically or differently one of the following groups

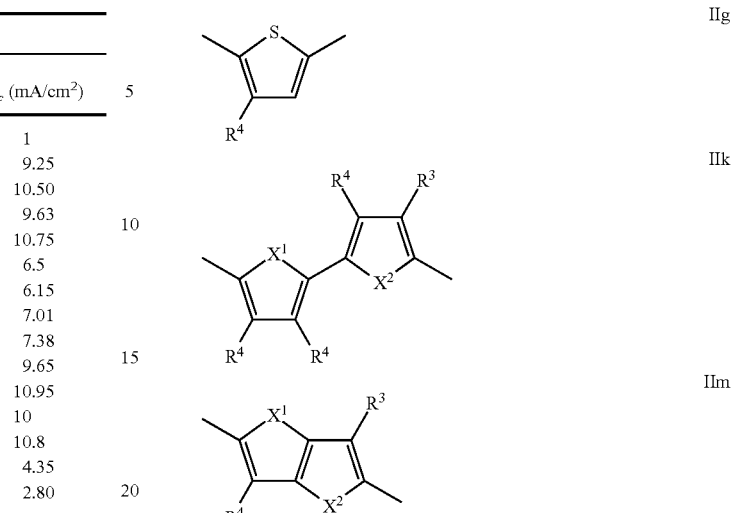

$X^1$ and $X^2$ are each S, $R^1$ and $R^2$ are on each occurrence identically or differently, and independently of each other, —CO—R$^y$, —CO—O—R$^y$, or —O—CO—R$^y$, R$^y$ is a straight-chain, branched or cyclic alkyl with 1 to 30 C atoms, in which one or more non-adjacent C atoms are optionally replaced by —O—, —S—, —CO—, —CO—O—, —O—CO—, —O—CO—O—, —CR$^0$=CR$^{00}$— or —C≡C— and in which one or more H atoms are optionally replaced by F, Cl, Br, I or CN, or is aryl or heteroaryl having 2 to 30 C atoms that is unsubstituted or substituted by one or more non-aromatic groups R$^5$, $R^3$ and $R^4$ on each occurrence identically or differently, and independently of each other, denote H, or primary alkyl, alkoxy or thiolakyl with 1 to 30 C atoms, or secondary alkyl, alkoxy or thioalkyl with 3 to 30 C atoms, or tertiary alkyl, alkoxy or thioalkyl with 4 to 30 C atoms, wherein in all these groups one or more H atoms are optionally replaced by F, or aryl, alkylated aryl or alkoxy aryl with 4 to 40 C atoms, $R^0$ and $R^{00}$ are independently of each other H or an optionally substituted carbyl or hydrocarbyl group optionally comprising one or more hetero atoms, Ar is benzo[2,1,3]thiadiazole-4,7-diyl, 5,6-dialkyl-benzo [2,1,3]thiadiazole-4,7-diyl, 5,6-dialkoxybenzo[2,1,3] thiadiazole-4,7-diyl, benzo[2,1,3]selenadiazole-4,7-diyl, 5,6-dialkoxy-benzo[2,1,3]selenadiazole-4,7-diyl, benzo[1,2,5]thiadiazole-4,7diyl, benzo[1,2,5]selenadiazole-4,7diyl, benzo[2,1,3]oxadiazole-4,7-diyl, 5,6-dialkoxybenzo[2,1,3]oxadiazole-4,7-diyl, 2H-benzotriazole-4,7-diyl, 2,3-dicyano-1,4-phenylene, 2,5-dicyano,1,4-phenylene, 2,3-difluro-1,4-phenylene, 2,5-difluoro,1,4-phenylene, 2,3,5,6-tetrafluoro,1,4-phenylene, 3,4-difluorothiophene-2,5-diyl, thieno[3,4-b]pyrazine-2,5-diyl, quinoxaline-5,8-diyl, thieno[3,4-b]thiophene-4,6-diyl, thieno[3,4-b]thiophene-6,4-diyl, or 3,6- pyrrolo[3,4-c]pyrrole-1,4-dione, all of which are unsubstituted, mono- or polysubstituted with halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR$^0$=CR$^{00}$— or —C≡C— and in which one or more H atoms are optionally replaced by F, Cl, Br, I or CN, or by an aryl, heteroaryl, aryloxy or heteroaryloxy group having 2 to 40 ring atoms that is unsubstituted or substituted by one or more non-aromatic groups $R^5$, and wherein "alkyl" means a straight-chain or branched alkyl group with 1 to 30 C atoms and "alkoxy" means a straight-chain or branched alkoxy group with 1 to 30 C atoms, $R^5$ is on each occurrence identically or differently H, halogen, —CN, —NC, —NCO, —NCS, —OCN, —SCN, —C(=O)NR°R°°, —C(=O)X°, —C(=O)R°, —NH$_2$, —NR°R°°, —SH, —SR°, —SO$_3$H, —SO$_2$R°, —OH, —NO$_2$, —CF$_3$, —SF$_5$, or optionally substituted silyl, carbyl or hydrocarbyl with 1 to 40 C atoms that is optionally substituted and optionally comprises one or more hetero atoms, X° is halogen, m is on each occurrence identically or differently 0 or 1, wherein in at least one repeating unit m is 1, o is on each occurrence identically or differently 0 or 1, wherein in at least one repeating unit o is 1, i and k are on each occurrence identically or differently, and independently of each other, 0 or 1, wherein in at least one repeating unit at least one of i and k is 1, and n is an integer >1.

2. The polymer according to claim 1, which is of the following formula

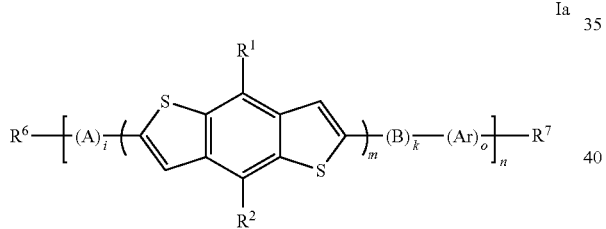

Ia wherein $R^{1-4}$, A, B, Ar, i, k, m, n and o on each occurrence identically or differently have the meanings given for the polymer of formula I, and $R^6$ and $R^7$ have independently of each other one of the meanings of $R^1$, or denote —CH$_2$Cl, —CHO, —CH=CH$_2$, —SiR'R"R'", —SnR'R"R'", —BR'R", —B(OR')(OR"), —B(OH)$_2$, or P-Sp, wherein P and Sp are as defined for the polymer of formula I, R', R" and R'" have independently of each other one of the meanings of H or an optionally substituted carbyl or hydrocarbyl group optionally comprising one or more hetero atoms, and R' and R" may also form a ring together with the hetero atom to which they are attached, and R°, R°° and $R^5$ are as defined for the polymer of formula I.

3. The polymer according to claim 1, wherein $R^1$ and $R^2$ denote —CO—R$^y$ or —CO—O—R$^y$, wherein R$^y$ is straight-chain, branched or cyclic alkyl with 1 to 30 C atoms, and wherein in all aforementioned groups one or more H atoms are optionally replaced by F.

4. The polymer according to claim 1, wherein $R^3$ and $R^4$ denote straight-chain or branched alkyl, alkoxy or thioalkyl with 1 to 15 C atoms, wherein one or more H atoms are optionally replaced by F.

5. The polymer according to claim 1, wherein $R^1$ and $R^2$ denote —CO—R$^y$ or —CO—O—R$^y$.

6. The polymer according to claim 1, wherein

Ar is on each occurrence identically or differently benzo[2,1,3]thiadiazole-4,7-diyl, 5,6-dialkyl-benzo[2,1,3]thiadiazole-4,7-diyl, 5,6-dialkoxybenzo[2,1,3]thiadiazole-4,7-diyl, benzo[2,1,3]selenadiazole-4,7-diyl, 5,6-dialkoxy-benzo[2,1,3]selenadiazole-4,7-diyl, benzo[1,2,5]thiadiazole-4,7,diyl, benzo[1,2,5]selenadiazole-4,7,diyl, benzo[2,1,3]oxadiazole-4,7-diyl, 5,6-dialkoxybenzo[2,1,3]oxadiazole-4,7-diyl, 2H-benzotriazole-4,7-diyl, 2,3-dicyano-1,4-phenylene, 2,5-dicyano,1,4-phenylene, 2,3-difluro-1,4-phenylene, 2,5-difluoro,1,4-phenylene, 2,3,5,6-tetrafluoro,1,4-phenylene, 3,4-difluorothiophene-2,5-diyl, thieno[3,4-b]pyrazine-2,5-diyl, quinoxaline-5,8-diyl, thieno[3,4-]thiophene-4,6-diyl, thieno[3,4-b]thiophene-6,4-diyl, or 3,6-pyrrolo[3,4-c]pyrrole-1,4-dione, all of which are substituted on each occurrence identically or differently, and independently of each other by one or more of the following groups: a straight-chain, branched or cyclic alkyl with 1 to 35 C atoms, in which one or more non-adjacent C atoms are optionally replaced by —O—, —S—, —CO—, —CO—O—, —O—CO—O—, —CR°=CR°°— or —C≡C— and in which one or more H atoms are optionally replaced by F, Cl, Br, I or CN.

7. The polymer according to claim 1, wherein

Ar is on each occurrence identically or differently benzo[2,1,3]thiadiazole-4,7-diyl, 5,6-dialkyl-benzo[2,1,3]thiadiazole-4,7-diyl, 5,6-dialkoxybenzo[2,1,3]thiadiazole-4,7-diyl, benzo[2,1,3]selenadiazole-4,7-diyl, 5,6-dialkoxy-benzo[2,1,3]selenadiazole-4,7-diyl, benzo[1,2,5]thiadiazole-4,7,diyl, benzo[1,2,5]selenadiazole-4,7,diyl, benzo[2,1,3]oxadiazole-4,7-diyl, 5,6-dialkoxybenzo[2,1,3]oxadiazole-4,7-diyl, 2H-benzotriazole-4,7-diyl, 2,3-dicyano-1,4-phenylene, 2,5-dicyano,1,4-phenylene, 2,3-difluro-1,4-phenylene, 2,5-difluoro,1,4-phenylene, 2,3,5,6-tetrafluoro,1,4-phenylene, 3,4-difluorothiophene-2,5-diyl, thieno[3,4-b]pyrazine-2,5-diyl, quinoxaline-5,8-diyl, thieno[3,4-b]thiophene-4,6-diyl, thieno[3,4-b]thiophene-6,4-diyl, or 3,6-pyrrolo[3,4-c]pyrrole-1,4-dione, all of which are substituted on each occurrence identically or differently, and independently of each other by one or more straight-chain alkoxy groups.

8. The polymer according to claim 1, wherein

Ar is

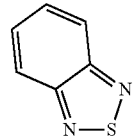

which is substituted on each occurrence identically or differently, and independently of each other by one or more straight-chain alkoxy groups.

9. A polymer, which is of one of the following formulae
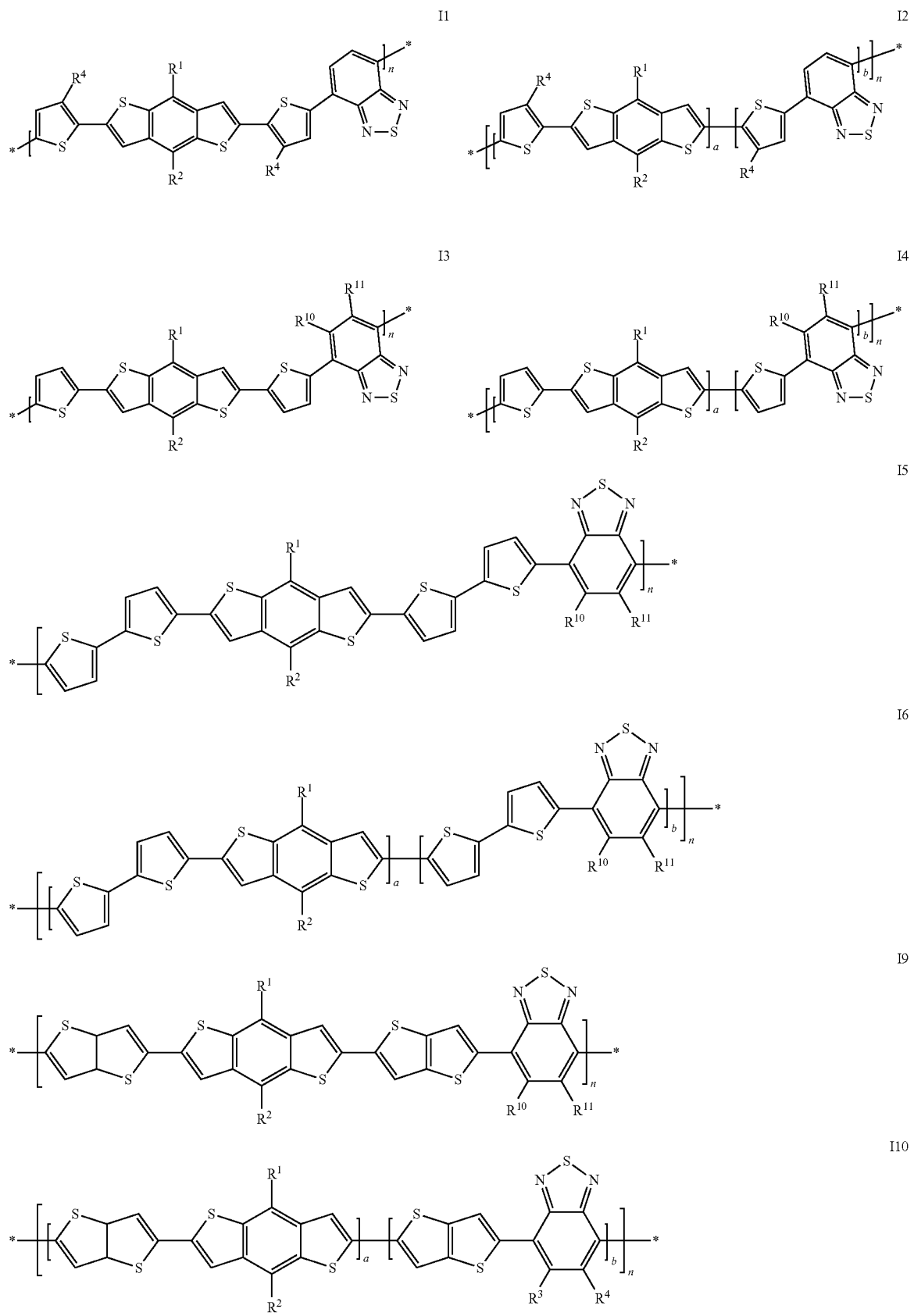

-continued
I11
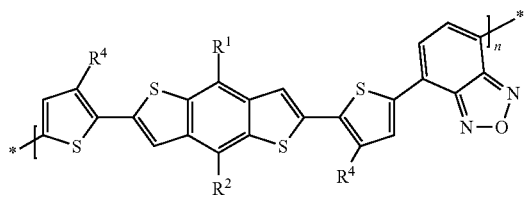
I12
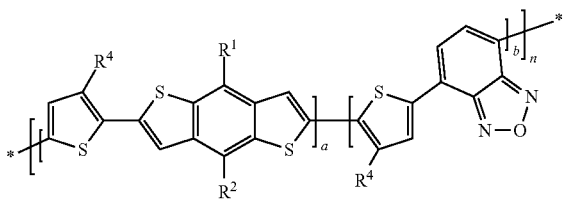
I13
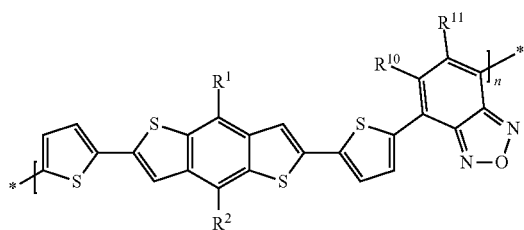
I14
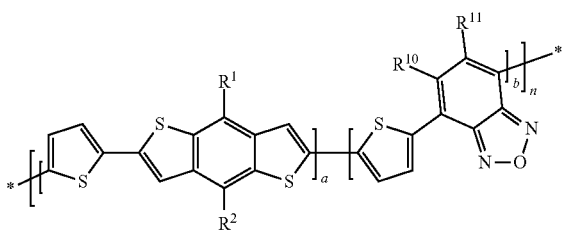
I15
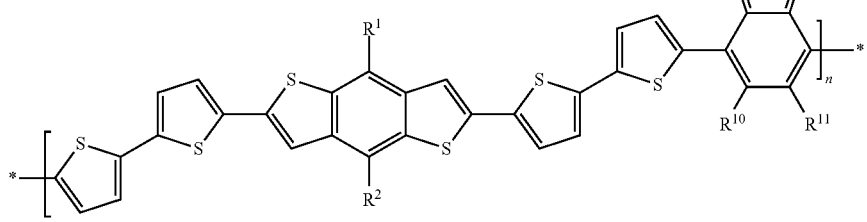
I16
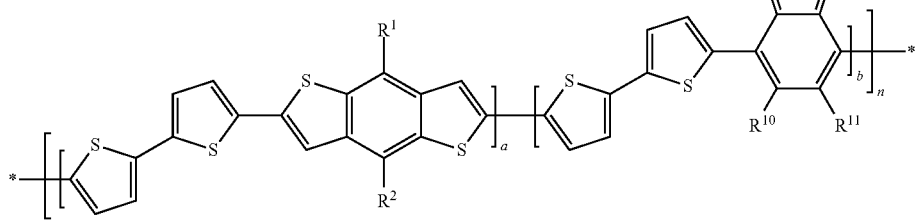
I19
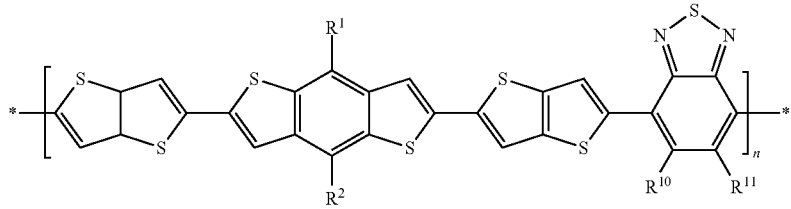
I20
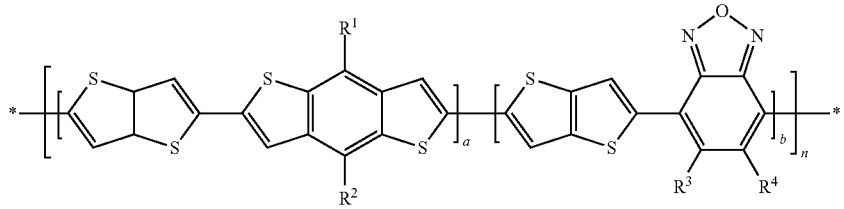
wherein
$R^1$ and $R^2$ are on each occurrence identically or differently, and independently of each other, —CO—$R^y$, —CO—O—$R^y$, or —O—CO—$R^y$,
$R^y$ is a straight-chain, branched or cyclic alkyl with 1 to 30 C atoms, in which one or more non-adjacent C atoms are optionally replaced by —O—, —S—, —CO—, —CO—O—, —O—CO—, —O—CO—

O—, —CR⁰═CR⁰⁰— or —C≡C— and in which one or more H atoms are optionally replaced by F, Cl, Br, I or CN, or is aryl or heteroaryl having 2 to 30 C atoms that is unsubstituted or substituted by one or more non-aromatic groups $R^5$, $R^3$ and $R^4$ on each occurrence identically or differently, and independently of each other, denote
primary alkyl, alkoxy or thiolalkyl with 1 to 30 C atoms, or secondary alkyl, alkoxy or thioalkyl with 3 to 30 C atoms, or tertiary alkyl, alkoxy or thioalkyl with 4 to 30 C atoms, wherein in all these groups one or more H atoms are optionally replaced by F, or
aryl, alkylated aryl or alkoxy aryl with 4 to 40 C atoms, $R^0$ and $R^{00}$ are independently of each other H or an optionally substituted carbyl or hydrocarbyl group optionally comprising one or more hetero atoms, $R^5$ is on each occurrence identically or differently H, halogen, —CN, —NC, —NCO, —NCS, —OCN, —SCN, —C(═O)NR⁰R⁰⁰, —C(═O)X⁰, —C(═O)R⁰, —NH₂, —NR⁰R⁰⁰, —SH, —SR⁰, —SO₃H, —SO₂R⁰, —OH, —NO₂, —CF₃, —SF₅, optionally substituted silyl, carbyl or hydrocarbyl with 1 to 40 C atoms that is optionally substituted and optionally comprises one or more hetero atoms, $X^0$ is halogen, n is an integer >1, and $R^{10}$ and $R^{11}$ have independently of each other one of the meanings of $R^1$ or denote primary alkyl, alkoxy or thioalkyl with 1 to 30 C atoms, or secondary alkyl, alkoxy or thioalkyl with 3 to 30 C atoms, or tertiary alkyl, alkoxy or thioalkyl with 4 to 30 C atoms, wherein in all these groups one or more H atoms are optionally replaced by F, or are aryl, alkylated aryl or alkoxy aryl with 4 to 40 C atoms, and wherein formula I2, I4, 6, I8, I10, I12, I14, I16, I18 and I20 denote random copolymers formed by units wherein a=1 and b=0 and units wherein a=0 and b=1.

10. A polymer blend comprising one or more polymers according to claim 1, and one or more further polymers, which are optionally selected from polymers having semiconducting, charge transport, hole/electron transport, hole/electron blocking, electrically conducting, photoconducting or light emitting properties.

11. A formulation comprising one or more polymers according to claim 1, and one or more solvents, which are optionally selected from organic solvents, and optionally one or more further polymers, which are optionally selected from polymers having semiconducting, charge transport, hole/electron transport, hole/electron blocking, electrically conducting, photoconducting or light emitting properties.

12. A charge transport, semiconducting, electrically conducting, photoconducting or light emitting material in optical, electrooptical, electronic, electroluminescent or photoluminescent component or device, comprising one or more polymers according to claim 1 and optionally one or more solvents, which are optionally selected from organic solvents, and optionally one or more further polymers, which are optionally selected from polymers having semiconducting, charge transport, hole/electron transport, hole/electron blocking, electrically conducting, photoconducting or light emitting properties.

13. An optical, electrooptical or electronic component or device comprising one or more polymers according to claim 1 and optionally one or more solvents, which are optionally selected from organic solvents, and optionally one or more further polymers, which are optionally selected from polymers having semiconducting, charge transport, hole/electron transport, hole/electron blocking, electrically conducting, photoconducting or light emitting properties.

14. The component or device according to claim 13, which is an organic field effect transistor (OFET), thin film transistor (TFT), integrated circuit (IC), logic circuit, capacitor, radio frequency identification (RFID) tag, organic light emitting diode (OLED), organic light emitting transistor (OLET), flat panel display, backlight of a display, organic photovoltaic device (OPV), solar cell, laser diode, photoconductor, photodetector, electrophotographic device, electrophotographic recording device, organic memory device, sensor device, charge injection layer, charge transport layer or interlayer in a polymer light emitting diode (PLEDs), Schottky diode, planarising layer, antistatic film, polymer electrolyte membrane (PEM), conducting substrate, conducting pattern, electrode material in a battery, alignment layer, biosensor, biochip, security marking, security device, or a component or device for detecting and/or discriminating DNA sequences.

15. The component or device according to claim 14, which is a bulk heterojunction OPV device.

16. A process of preparing a polymer according to claim 1, comprising coupling one or more identical or different monomers of formula IIIa

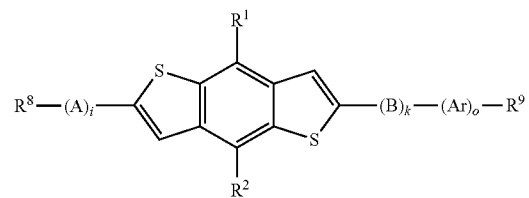

wherein $R^1$, $R^2$, A, B and Ar have the meanings given for the polymer of formula I, $R^8$ and $R^9$ are, on each occurrence identically or differently, and independently of each other, halogen, a straight-chain, branched or cyclic alkyl with 1 to 35 C atoms, in which one or more non-adjacent C atoms are optionally replaced by —O—, —S—, —CO—, —CO—O—, —O—CO—O—, —CR⁰═CR⁰⁰— or —C≡C— and in which one or more H atoms are optionally replaced by F, Cl, Br, I or CN, or an aryl, heteroaryl, aryloxy or heteroaryloxy group having 2 to 40 ring atoms that is unsubstituted or substituted by one or more non-aromatic groups $R^5$, or are —CH₂Cl, —CHO, —CH═CH₂, —SiR'R"R'", —SnR'R"R'", —BR'R", —B(OR')(OR"), —B(OH)₂, P-Sp, Cl, Br, I, O-tosylate, O-triflate, O-mesylate, O-nonaflate, —SiMe₂F, —SiMeF₂, —O—SO₂Z¹, —B(OZ²)₂, —CZ³═C(Z³)₂, —C≡CH or —Sn(Z⁴)₃, P, Sp, $R^0$, $R^{00}$ and $R^5$ are as defined for the polymer of formula I, R', R"R'" have independently of each other one of the meanings of H or an optionally substituted carbyl or hydrocarbyl group optionally comprising one or more hetero atoms, and R'and R" may also form a ring together with the hetero atom to which they are attached, $Z^{1-4}$ are each independently an alkyl or aryl, each being optionally substituted, or two groups $Z^2$ form a cyclic group, o is 0, and i and k are independently of each other 0 or 1, with one or more identical or different comonomers of the formula $$R^8—Ar—R^9 \qquad (5)$$

and optionally one or more identical or different comonomers selected from the following formulae $$R^8\text{-A-}R^9$$

$$R^8—B—R^9 \qquad (10)$$

in an aryl-aryl coupling reaction.

\* \* \* \* \*